(12) United States Patent
Purdon et al.

(10) Patent No.: US 10,383,574 B2
(45) Date of Patent: Aug. 20, 2019

(54) SYSTEMS AND METHODS TO INFER BRAIN STATE DURING BURST SUPPRESSION

(71) Applicants: Patrick L. Purdon, Somerville, MA (US); Emery N. Brown, Boston, MA (US); Laura D. Lewis, Cambridge, MA (US); Brandon M. Westover, Belmont, MA (US); ShiNung Ching, Cambridge, MA (US)

(72) Inventors: Patrick L. Purdon, Somerville, MA (US); Emery N. Brown, Boston, MA (US); Laura D. Lewis, Cambridge, MA (US); Brandon M. Westover, Belmont, MA (US); ShiNung Ching, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 1209 days.

(21) Appl. No.: 14/318,277

(22) Filed: Jun. 27, 2014

(65) Prior Publication Data
US 2015/0011907 A1 Jan. 8, 2015

Related U.S. Application Data

(60) Provisional application No. 61/841,165, filed on Jun. 28, 2013.

(51) Int. Cl.
*A61B 5/0476* (2006.01)
*A61B 5/00* (2006.01)
(Continued)

(52) U.S. Cl.
CPC .......... *A61B 5/6814* (2013.01); *A61B 5/0478* (2013.01); *A61B 5/4821* (2013.01); *A61B 5/4839* (2013.01); *A61B 5/4064* (2013.01)

(58) Field of Classification Search
None
See application file for complete search history.

(56) References Cited

U.S. PATENT DOCUMENTS 2,507,631 A 5/1950 Hartmann et al.
2,957,880 A 10/1960 Rometsch
(Continued)

FOREIGN PATENT DOCUMENTS

EP 0765630 A1 4/1997
JP 2008178546 A 8/2008
(Continued)

OTHER PUBLICATIONS

Absalom, et al., Closed-Loop Control of Anesthesia Using Bispectral Index, Anesthesiology, 2002, 96(1):67-73.
(Continued)

*Primary Examiner* — Etsub D Berhanu
(74) *Attorney, Agent, or Firm* — Quarles & Brady LLP

(57) ABSTRACT

Systems and methods are provided for monitoring a subject, and particularly, for inferring an underlying brain state present in absence of current conditions. In some aspects, a method for monitoring the subject is provided including steps of receiving physiological feedback from at least one sensor configured to acquire physiological information from locations associated with a subject's brain, assembling a set of time-series data using the received physiological feedback, and identifying portions of the set of time-series data that indicate a burst suppression state. The method also includes identifying a burst characteristic profile associated with a burst pattern determined from the identified portions, and comparing the burst characteristic against a reference set of burst profiles. The method further includes determining, based on the comparison, a likelihood of a brain state of the subject underlying the burst suppression state, and generat-
(Continued)

ing a report indicative of the likelihood of the determined brain state.

**16 Claims, 19 Drawing Sheets
(10 of 19 Drawing Sheet(s) Filed in Color)**

(51) Int. Cl.
*A61B 5/0478* (2006.01)
*A61B 5/04* (2006.01)

(56) References Cited

U.S. PATENT DOCUMENTS

| | | | |
|---|---|---|---|
| 4,195,643 A | 4/1980 | Pratt, Jr. | |
| 4,392,849 A | 7/1983 | Petre et al. | |
| 4,448,199 A | 5/1984 | Schmid | |
| 4,911,167 A | 3/1990 | Corenman et al. | |
| 5,195,530 A | 3/1993 | Shindel | |
| 5,357,976 A * | 10/1994 | Feng | A61B 5/04004 600/544 |
| 5,851,438 A | 12/1998 | Chan | |
| 5,908,850 A | 6/1999 | Leitlin et al. | |
| 6,025,362 A | 2/2000 | Fukunaga et al. | |
| 6,032,063 A | 2/2000 | Hoar et al. | |
| 6,032,065 A | 2/2000 | Brown | |
| 6,067,467 A | 5/2000 | John | |
| 6,281,242 B1 | 8/2001 | Regan et al. | |
| 6,338,713 B1 | 1/2002 | Chamoun et al. | |
| 6,708,051 B1 | 3/2004 | Durousseau | |
| 6,740,214 B1 | 5/2004 | Dobson et al. | |
| 6,944,565 B2 | 9/2005 | Meneilage et al. | |
| 7,006,872 B2 | 2/2006 | Gielen et al. | |
| 7,286,871 B2 | 10/2007 | Cohen | |
| 7,783,343 B2 | 8/2010 | Sarkela et al. | |
| 8,025,404 B2 | 9/2011 | Bolger et al. | |
| 8,073,534 B2 | 12/2011 | Low | |
| 8,244,526 B2 | 8/2012 | Vos et al. | |
| 8,298,154 B2 | 10/2012 | Hete et al. | |
| 8,315,970 B2 | 11/2012 | Lalay et al. | |
| 8,521,294 B2 | 8/2013 | Sarma et al. | |
| 8,630,722 B2 | 1/2014 | Condurso et al. | |
| 2002/0017296 A1* | 2/2002 | Hickle | A61B 5/417 128/203.12 |
| 2002/0059159 A1* | 5/2002 | Cook | A61B 5/04012 706/62 |
| 2002/0128798 A1 | 9/2002 | Lange et al. | |
| 2002/0156357 A1 | 10/2002 | Axelgaard | |
| 2002/0188211 A1* | 12/2002 | Voith | A61B 5/0205 600/509 |
| 2003/0088167 A1 | 5/2003 | Fendrock et al. | |
| 2003/0130585 A1 | 7/2003 | Wenger | |
| 2004/0079372 A1* | 4/2004 | John | A61B 5/048 128/204.18 |
| 2004/0138579 A1* | 7/2004 | Deadwyler | A61B 5/04001 600/544 |
| 2004/0143021 A1 | 7/2004 | Larijani | |
| 2004/0171959 A1* | 9/2004 | Stadler | A61N 1/3622 600/518 |
| 2004/0193068 A1 | 9/2004 | Burton et al. | |
| 2005/0054941 A1 | 3/2005 | Ting et al. | |
| 2005/0131476 A1* | 6/2005 | Kim | A61B 5/04525 607/27 |
| 2005/0137494 A1* | 6/2005 | Viertio-Oja | A61B 5/048 600/544 |
| 2006/0009733 A1* | 1/2006 | Martin | A61B 5/4821 604/65 |
| 2006/0135880 A1 | 6/2006 | Sarkela | |
| 2006/0178585 A1 | 8/2006 | Sharrock | |
| 2006/0229519 A1 | 10/2006 | Fujiwara et al. | |
| 2007/0067003 A1 | 3/2007 | Sanchez et al. | |
| 2007/0073355 A1 | 3/2007 | Dilorenzo | |
| 2007/0100389 A1 | 5/2007 | Jaax et al. | |
| 2007/0123468 A1 | 5/2007 | Jenkins | |
| 2007/0150025 A1 | 6/2007 | Dilorenzo et al. | |
| 2007/0167694 A1 | 7/2007 | Causevic et al. | |
| 2007/0191704 A1 | 8/2007 | DeCharms | |
| 2007/0203540 A1 | 8/2007 | Goetz et al. | |
| 2008/0021345 A1 | 1/2008 | Kern et al. | |
| 2008/0249431 A1* | 10/2008 | Bier | A61B 5/04012 600/544 |
| 2008/0306397 A1 | 12/2008 | Bonmassar et al. | |
| 2010/0023089 A1 | 1/2010 | DiLorenzo | |
| 2010/0280333 A1 | 11/2010 | Parshuram et al. | |
| 2011/0044524 A1 | 2/2011 | Wang et al. | |
| 2011/0082381 A1 | 4/2011 | Othman et al. | |
| 2011/0125046 A1 | 5/2011 | Burton et al. | |
| 2011/0137134 A1 | 6/2011 | Hemmerling et al. | |
| 2011/0137297 A1 | 6/2011 | Kiani et al. | |
| 2011/0218454 A1 | 9/2011 | Low | |
| 2011/0224570 A1 | 9/2011 | Causevic | |
| 2012/0022391 A1 | 1/2012 | Leuthardt | |
| 2012/0029378 A1 | 2/2012 | Low | |
| 2012/0101401 A1 | 4/2012 | Faul et al. | |
| 2012/0250963 A1 | 10/2012 | Carroll et al. | |
| 2013/0131464 A1 | 5/2013 | Westbrook et al. | |
| 2013/0197339 A1 | 8/2013 | Bardakjian et al. | |
| 2013/0211224 A1 | 8/2013 | Isenhart et al. | |
| 2013/0310422 A1 | 11/2013 | Brown et al. | |
| 2013/0331660 A1 | 12/2013 | Al-Ali et al. | |
| 2014/0012100 A1 | 1/2014 | Al-Ali et al. | |
| 2014/0180160 A1 | 6/2014 | Brown et al. | |
| 2014/0187973 A1 | 7/2014 | Brown et al. | |
| 2014/0316217 A1 | 10/2014 | Purdon et al. | |
| 2014/0316218 A1 | 10/2014 | Purdon et al. | |
| 2014/0323897 A1 | 10/2014 | Brown et al. | |
| 2014/0323898 A1 | 10/2014 | Purdon et al. | |
| 2014/0371548 A1 | 12/2014 | Al-Ali et al. | |
| 2015/0011907 A1 | 1/2015 | Purdon et al. | |
| 2015/0080754 A1 | 3/2015 | Purdon et al. | |

FOREIGN PATENT DOCUMENTS

| | | |
|---|---|---|
| RU | 95243 U1 | 6/2010 |
| WO | 2004036379 A2 | 4/2004 |
| WO | 2004037114 A2 | 5/2004 |
| WO | 2004047632 A1 | 6/2004 |
| WO | 2012145285 A1 | 10/2012 |
| WO | 2012154701 A1 | 11/2012 |

OTHER PUBLICATIONS

Absalom, et al., Closed Loop Anesthesia: Are We Getting Close to Finding the Holy Grail?, Anesthesia & Analgesia, 2011, 112(3):516-518.
Andrews, et al., The Chronux Manual, Aug. 16, 2008, 178 pages.
Araki, et al., Computer Control of Physiological States of Patients Under and After Surgical Operation, Annual Reviews in Control, 2005, 29:229-236.
Barras, et al., Total Intravenous Anesthesia on the Battlefield, The Army Medical Department Journal, 2009, pp. 68-72.
Bellville, et al., Servo Control of General Anesthesia, Science, 1957, 126:827-830.
Besch, et al., Occurrence of and Risk Factors for Electroencephalogram Burst Suppression During Propofol-Remifentanil Anaesthesia, British Journal of Anaesthesia, Advance Access Published Aug. 8, 2011, 8 pages.
Besthorn, et al., EEG Coherence in Alzheimer Disease, Electroencephalography and Clinical Neurophysiology, 1994, 90:242-245.
Bickford, Automatic Electroencephalographic Control of General Anesthesia, EEG Clin. Neurophysiol., 1950, 2:93-96.
Bickford, Use of Frequency Discrimination in the Automatic Electroencephalographic Control of Anesthesia (Servo-Anesthesia), EEG Clin. Neurophysiol., 1951, 3:83-86.
Blanco, et al., Time-Frequency Analysis of Electroencephalogram Series. III. Wavelet Packets and Information Cost Function, Physical Review E, 1998, 57(1):932-940.
Bonmassar, Resistive Tapered Stripline (RTS) in Electroencephalogram Recordings During MRI, IEEE Transactions on Microwave Theory and Techniques, 2004, 52(8):1992-1998.

(56) References Cited

OTHER PUBLICATIONS

Bourguignon, et al., A Sparsity-Based Method for the Estimation of Spectral Lines From Irregularly Sampled Data, IEEE Journal of Selected Topics in Signal Processing, 2007, 1(4):575-585.
Breshears, et al., Stable and Dynamic Cortical Electrophysiology of Induction and Emergence with Propofol Anesthesia, PNAS, 2010, 107(49):21170-21175.
Candes, et al., Enhancing Sparsity by Reweighted l1 Minimization, J. Fourier Anal. Appl., 2008, 14:877-905.
Chemali, et al., Burst Suppression Probability Algorithms: State-Space Methods for Tracking EEG Burst Suppression, J. Neural. Eng., 2013, 10(5):056017.
Ching, et al., A Neurophysiological-Metabolic Model for Burst Suppression, PNAS, 2012, 109(8):3095-3100.
Cimenser, et al., Tracking Brain States Under General Anesthesia by Using Global Coherence Analysis, PNAS, 2011, 108(21):8832-8837.
Ciuciu, et al., A Half-Quadratic Block-Coordinate Descent Method for Spectral Estimation, Signal Processing, 2002, 82:941-959.
Cotten, et al., Closed-Loop Continuous Infusions of Etomidate and Etomidate Analogs in Rats, Anesthesiology, 2011, 115(4):764-773.
Dodson, et al., Postoperative Effects of Methylphenidate, British Journal of Anaesthesia, 1980, 52:1265-1270.
Gentilini, et al., Modeling and Closed-Loop Control of Hypnosis by Means of Bispectral Index (BIS) with Isoflurane, IEEE Transactions on Biomedical Engineering, 2001, 48(8):874-889.
Glass, Automated Control of Anesthesia Ten Years Later: Futuristic Novelty or Present Day Reality, Can. J. Anesth./J. Can. Anesth., 2010, 57:715-719.
Goldman, et al., Acquiring Simultaneous EEG and Functional MRI, Clinical Neurophysiology, 2000, 111:1974-1980.
Hahn, et al., Closed-Loop Anesthetic Drug Concentration Estimation Using Clinical-Effect Feedback, IEEE Transactions on Biomedical Engineering, 2011, 58(1):3-6.
Hahn, et al., A Direct Dynamic Dose-Response Model of Propofol for Individualized Anesthesia Care, Journal of Latex Class Files, 2007, 6(1):1-8.
Hemmerling, et al., A Randomized Controlled Trial Demonstrates that a Novel Closed-Loop Propofol System Performs Better Hypnosis Control than Manual Administration, Can. J. Anesth./J. Can. Anesth., 2010, 57:725-735.
John, et al., Invariant Reversible QEEG Effects of Anesthetics, Consciousness and Cognition, 2001, 10:165-183.
Lemieux, et al., Recording of EEG During fMRI Experiments: Patient Safety, MRM, 1997, 38:943-952.
Leslie, et al., Closed Loop Control of Sedation for Colonoscopy Using the Bispectral Index, Anaesthesia, 2002, 57:690-709.
Liley, et al., Propofol and Remifentanil Differentially Modulate Frontal Electroencephalographic Activity, Anesthesiology, 2010, 113:292-304.
Lin, et al., EEG-Based Drowsiness Estimation for Safety Driving Using Independent Component Analysis, IEEE Transactions on Circuits and Systems-I: Regular Papers, 2005, 52(12):2726-2738.
Liu, et al., Titration of Propofol for Anesthetic Induction and Maintenance Guided by the Bispectral Index: Closed-Loop Versus Manual Control, Anesthesiology, 2006, 104:686-695.
Liu, et al., Feasibility of Closed-Loop Titration of Propofol Guided by the Bispectral Index for General Anaesthesia Induction: A Prospective Randomized Study, European Journal of Anaesthesiology, 2006, 23:465-469.
Liu, et al., Neural Origin of Spontaneous Hemodynamic Fluctuations in Rats Under Burst-Suppression Anesthesia Condition, Cerebral Cortex, 2011, 21:374-384.
Locher, et al., A New Closed-Loop Control System for Isoflurane Using Bispectral Index Outperforms Manual control, Anesthesiology, 2004, 101:591-602.
Lotte, et al., A Review of Classification Algorithms for EEG-Based Brain-Computer Interfaces, Journal of Neural Engineering, 2007, 4:R1-R13.

Martin, et al., Investigating Neural-Hemodynamic Coupling and the Hemodynamic Response Function in the Awake Rat, NeuroImage, 2006, 32:33-48.
Mirsattari, et al., Treatment of Refractory Status Epilepticus With Inhalational Anesthetic Agents Isoflurane and Desflurane, Arch. Neurol., 2004, 61:1254-1259.
Molaee-Ardekani, et al., Delta Waves Differently Modulate High Frequency Components of EEG Oscillations in Various Unconsciousness Levels, Proceedings of the 29th Annual International Conference of the IEEE EMBS, 2007, pp. 1294-1297.
Morley, et al., Closed Loop Control of Anaesthesia: An Assessment of the Bispectral Index as the Target of Control, Anaesthesia, 2000, 55:953-959.
Mortier, et al., Closed-Loop Controlled Administration of Propofol Using Bispectral Analysis, Anesthesia, 1998, 53:749-754.
Orsini, et al., Propofol Infusion Syndrome: Case Report and Literature Review, Am. J. Health-Syst. Pharm., 2009, 66:908-915.
Pritchett, et al., Power Analysis of Gamma Frequencies (30-47Hz), Adjusting for Muscle Activity (80-97Hz), in Anesthesia: A Comparison Between Young Adults, Middle-Aged and the Elderly, 30th Annual International IEEE EMBS Conference, 2008, pp. 825-830.
Purdon, Multimodal Neuroimaging with Simultaneous Electroencephalogram and High-Field Functional Magnetic Resonance Imaging, Master Thesis Submitted to the Harvard-MIT Division of Health Sciences and Technology, Jun. 2005.
Purdon, et al., Electroencephalogram Signatures of Loss and Recovery of Consciousness from Propofol, PNAS, Published Online Mar. 4, 2013, pp. E1142-E1151.
Puri, et al., Closed-Loop Anaesthesia Delivery System (CLADS(TM)) Using Bispectral Index: A Performance Assessment Study, Anaesthesia and Intensive Care, 2007, 35(3):357-362.
Roche-Labarbe, et al., Coupled Oxygenation Oscillation Measured by Nirs and Intermittent Cerebral Activation on EEG in Premature Infants, NeuroImage, 2007, 36:718-727.
Rossetti, et al., Refractory Status Epilepticus, Effect of Treatment Aggressiveness on Prognosis, Arch. Neurol., 2005, 62:1698-1702.
Sacchi, et al., Interpolation and Extrapolation Using a High-Resolution Discrete Fourier Transform, IEEE Transactions on Signal Processing, 1998, 46(1)31-38.
Sartori, et al., On-Line Estimation of Propofol Pharmacodynamic Parameters, Proceedings of the 2005 IEEE Engineering in Medicine and Biology 27th Annual Conference, 2005, pp. 74-77.
Sawaguchi, et al., A Model-Predictive Hypnosis Control System Under Total Intravenous Anesthesia, IEEE Transactions on Biomedical Engineering, 2008, 55(3):874-887.
Schaffer, et al., The Effect of the Atmosphere and the Role of Pore Filling on the Sintering of Aluminum, Acta Materialia, 2006, 54(1):131-138.
Schwilden, et al., Closed-Loop Feedback Control of Methohexital Anesthesia by Quantitative EEG Analysis in Humans, Anesthesiology, 1987, 67:341-347.
Schwilden, et al., Closed-Loop Feedback Control of Propofol Anaesthesia by Quantitative EEG Analysis in Humans, Br. J. Anaesth., 1989, 62:290-296.
Struys, et al., Comparison of Closed-Loop Controlled Administration of Propofol Using Bispectral Index as the Controlled Variable Versus "Standard Practice" Controlled Administration, Anesthesiology, 2001, 95(1):6-17.
Struys, et al., Closed Loops in Anaesthesia, Best Practice & Research Clinical Anaesthesiology, 2006, 20(1):211-220.
Tan, et al., Sparse Learning Via Iterative Minimization With Application to MIMO Radar Imaging, IEEE Transactions on Signal Processing, 2011, 59(3)1088-1101.
Truccolo, et al., A Point Process Framework for Relating Neural Spiking Activity to Spiking History, Neural Ensemble, and Extrinsic Covariate Effects, J. Neurophysiol., 2005, 93:1074-1089.
Van Vugt, Comparison of Spectral Analysis Methods for Characterizing Brain Oscillations, J. Neurosci. Methods, 2007, 162(1-2):49-63.
Vijn, et al., I.v. Anaesthesia and EEG Burst Suppression in Rats: Bolus Injections and Closed-Loop Infusions, British Journal of Anaesthesia, 1998, 81:415-421.

(56) References Cited

OTHER PUBLICATIONS

Vusanovic, et al., Microsegregation Phenomena in Al-Cu-Mg Alloy with Considering of Diffusion Phenomena in Primary Phase, Facta Universitatis, Series: Mechanical Engineering, 2001, 1(8):965-980.
Wang, et al., Precipitates and Intermetallic Phases in Precipitation and Hardening Al-Cu-Mg-(Li) Based Alloys, International Materials Reviews, 2005, 50(4):193-215.
Zdunek, et al., Improved M-FOCUSS Algorithm With Overlapping Blocks for Locally Smooth Sparse Signals, IEEE Transactions on Signal Processing, 2008, 56(10):4752-4761.
Article: "Polyesters", http://web.archive.org/web/20020812093256/http://pslc.ws/macrog/pet.htm, Copyright 1995, 1996 Department of Polymer Science, University of Southern Mississippi, 4 pages.
European Patent Office, Extended European Search Report, Application No. 12781958.9, dated Sep. 15, 2014, 12 pages.
PCT International Search Report and Written Opinion, PCT/US2005/042401, dated Jun. 14, 2006, 17 pages.
PCT International Search Report and Written Opinion, PCT/US2009/062072, dated May 12, 2010, 13 pages.
PCT International Search Report and Written Opinion, PCT/US2011/050213, dated May 1, 2012, 12 pages.
PCT International Search Report and Written Opinion, PCT/US2012/036854, dated Aug. 16, 2012, 6 pages.
PCT International Search Report and Written Opinion, PCT/US2013/064852, dated Jan. 23, 2014, 6 pages.
PCT International Search Report and Written Opinion, PCT/US2014/033619, dated Sep. 23, 2014, 12 pages.
PCT International Search Report and Written Opinion, PCT/US2014/035166, dated Aug. 29, 2014, 17 pages.
PCT International Search Report and Written Opinion, PCT/US2014/035178, dated Sep. 15, 2014, 15 pages.
PCT International Search Report and Written Opinion, PCT/US2014/035319, dated Sep. 26, 2014, 15 pages.
PCT International Search Report and Written Opinion, PCT/US2014/035329, dated Sep. 26, 2014, 11 pages.
PCT International Search Report and Written Opinion, PCT/US2014/035333, dated Sep. 26, 2014, 14 pages.
PCT International Search Report and Written Opinion, PCT/US2014/044692, dated Nov. 4, 2014, 12 pages.
PCT International Search Report and Written Opinion, PCT/US2014/044720, dated Nov. 28, 2014, 13 pages.
PCT International Search Report and Written Opinion, PCT/US2014/055509, dated Dec. 2, 2014, 15 pages.
PCT International Search Report and Written Opinion, PCT/US2014/064144, dated Jan. 27, 2015, 7 pages.

* cited by examiner

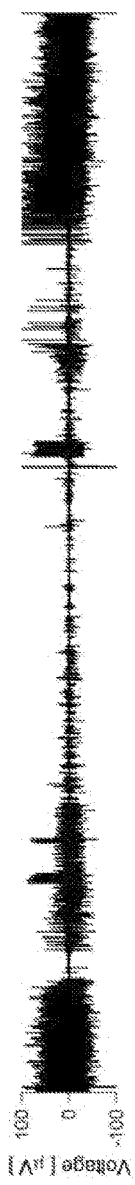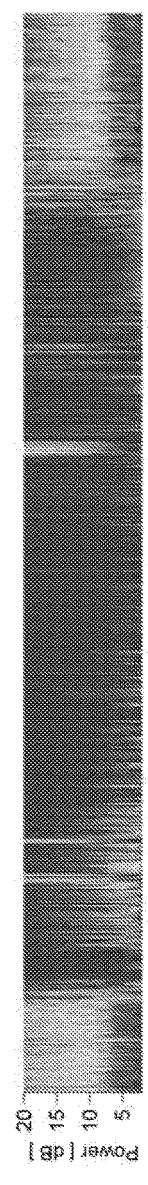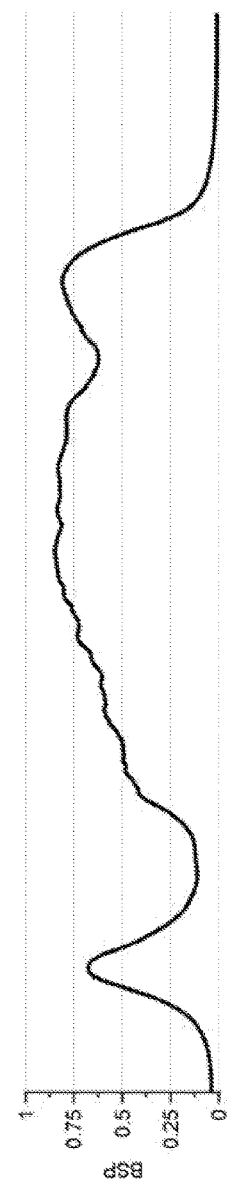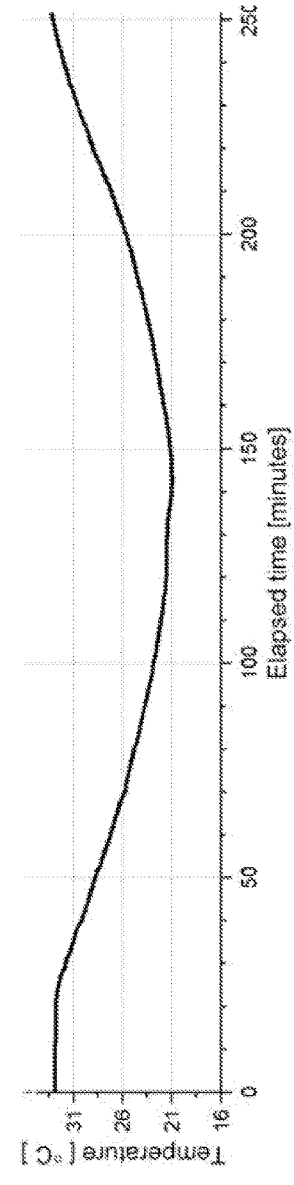

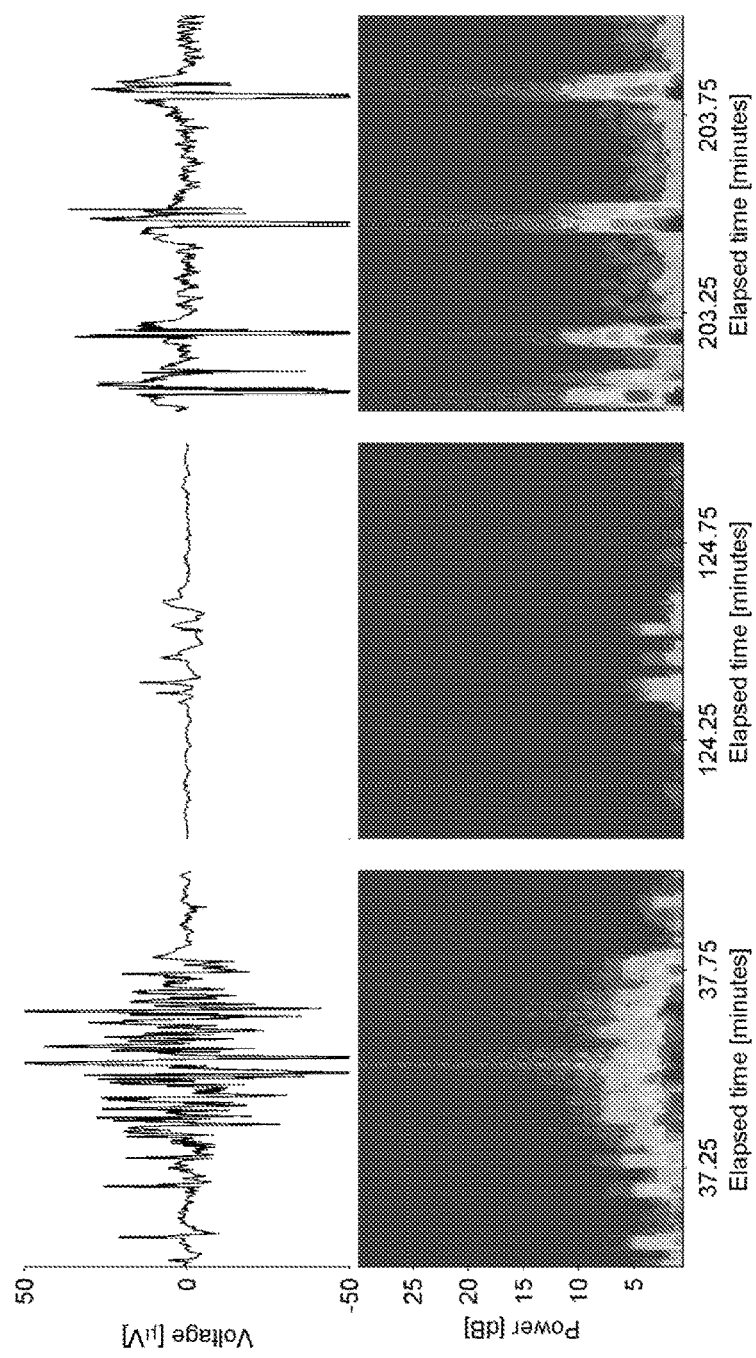

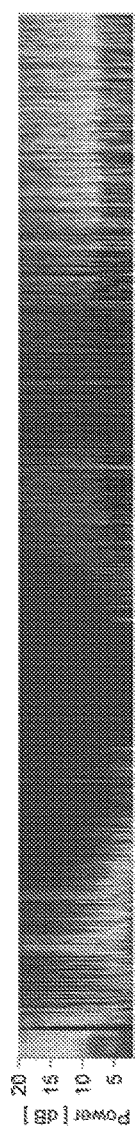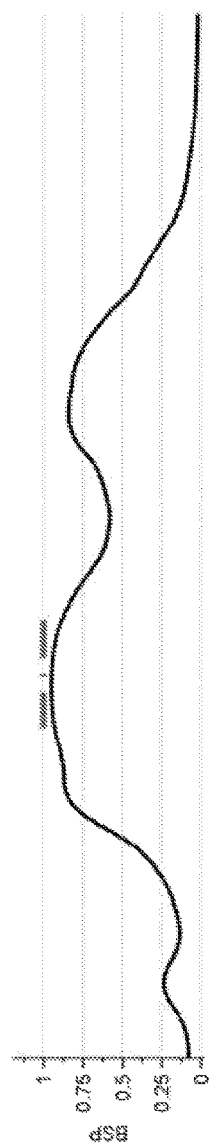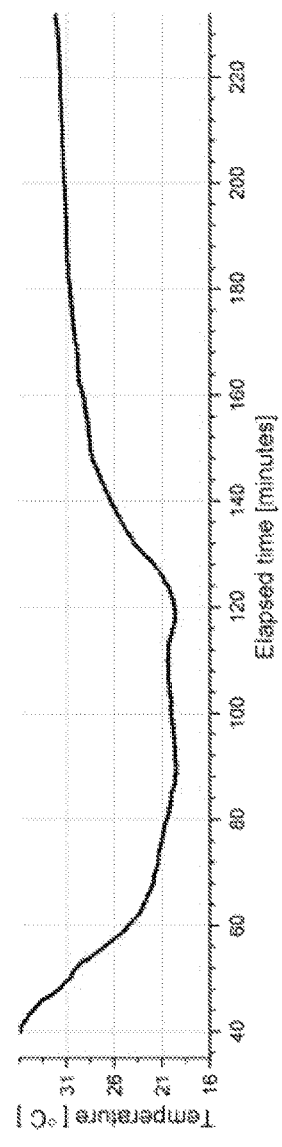
FIG. 14A
FIG. 14B
FIG. 14C
FIG. 14D
FIG. 14E

SYSTEMS AND METHODS TO INFER BRAIN STATE DURING BURST SUPPRESSION

The present application is based on, claims priority to, and incorporates herein by reference in its entirety U.S. provisional Application Ser. No. 61/841,165 filed Jun. 28, 2013, and entitled "SYSTEM AND METHOD TO INFER BRAIN STATE DURING BURST SUPPRESSION."

STATEMENT REGARDING FEDERALLY SPONSORED RESEARCH

This invention was made with government support under DP2OD006454, DP1OD003646, 1R01GM104948, awarded by the National Institutes of Health. The government has certain rights in the invention.

BACKGROUND OF THE INVENTION

The present disclosure relates to systems and methods for monitoring a subject. Specifically, the present disclosure relates to systems and methods for directly determining brain states, as well as inferring underlying brain states that would be present in absence of current conditions, by way of analyzing physiological feedback, such as electroencephalogram ("EEG") data associated with burst suppression states.

Since 1846 and the first public uses of ether as a means to control pain during surgical procedures, anesthesia, analgesics, and other administered compounds to control pain have been a mainstay of medicine. However, while the use of the anesthetic and the number of compounds with anesthetic properties in clinical use have grown astronomically since the initial uses of ether, the scientific understanding of the operation of the body when under anesthesia is still developing. For example, a complete understanding of the effects of anesthesia on patients and operation of the patient's brain over the continuum of "levels" of anesthesia is still lacking. As such, anesthesiologists are trained to recognize the effects of anesthesia and extrapolate an estimate of the "level" of anesthetic influence on a given patient based on the identified effects of the administered anesthesia.

Unfortunately, there are a great number of variables that can influence the effects, effectiveness, and, associated therewith, the "level" of anesthetic influence on a given patient. Some clear variables include physical attributes of the patient, such as age, state of general health, height, or weight, but also less obvious variables that are extrapolated, for example, based on prior experiences of the patient when under anesthesia. When these variables are compounded with the variables of a given anesthesiologists' practices and the variables presented by a particular anesthetic compound or, more so, combination of anesthetic compounds, the proper and effective administration of anesthesia to a given patient can appear to be an art and a science.

The anesthetized brain, though profoundly inactivated, is characterized by rich electrophysiological dynamics. At deep levels of anesthesia, the brain reaches a state of burst suppression. Burst suppression is an electroencephalogram pattern that consists of a quasi-periodic alternation between isoelectric quiescence (suppressions) lasting seconds or minutes as the brain becomes more inactivated, and high-voltage brain activity (bursts). Burst suppression appears to be a fundamental characteristic of the deeply anesthetized brain, and can also occur in a range of conditions including hypothermia, deep general anesthesia, certain infant encephalopathy and coma. It is also used in neurology as an electrophysiological endpoint in pharmacologically induced coma for brain protection after traumatic injury and during status epilepticus. However, despite the presence of burst suppression in this broad range of inactivated brain states, its biophysical mechanisms are poorly understood.

Classically, burst suppression has been regarded as a homogenous brain state. This perspective has been derived from EEG studies that burst and suppressions have been shown to occur concurrently across the scalp. However, because scalp EEG is spatially blurred, the underlying dynamics are not fully understood. In vivo studies in anesthetized animals have helped to identify the potential cellular correlates of burst suppression, showing that although nearly all cortical neurons are inhibited during suppression periods, a subset of thalamocortical neurons can continue firing at delta frequencies.

In search of a more detailed and complete mechanistic understanding, recent studies have shown that burst suppression is associated with enhanced excitability in cortical networks. These studies implicate extracellular calcium as a correlate for the switches between burst and suppression. A recent study has proposed an alternative mechanism, using computational methods, where burst suppression manifests in a state of reduced neuronal activity and cerebral metabolism. In such a state, insufficient production of adenosine triphosphate ("ATP") in local cortical networks can gate neuronal potassium channels, leading to suppression of action potentials. Such a mechanism accounts for the general features of burst suppression previously observed, as well as its occurrence under multiple etiologies, and also predicts a specific frequency structure for the neuronal activity within each burst.

Thus, as can be appreciated, the underlying phenomenon and, hence, a more encompassing understanding of just one brain state, represented by or correlated with burst suppression, is lacking. As such, the ability to accurately discern the current or predict a future state of the individual based on the observed physiological tracking information, such as elicited by EEG data, has been elusive.

Therefore, it would be desirable to have a system and method to determine or predict a current and/or future state of a subject, based on physiological tracking or monitoring information.

SUMMARY OF THE INVENTION

The disclosure overcomes the aforementioned drawbacks by providing systems and methods directed to neurophysiological dynamics of cortical circuits driving various physiological states in a subject's brain. Specifically, the present disclosure is directed to analysis of physiological data across multiple cortical sites, for example, in a substantially simultaneous fashion, to reveal spatial and temporal brain activity patterns across the human cortex. Therefore, as will be described, the present disclosure recognizes complexities associated with burst suppression states of a subject, which go beyond presently accepted understanding, and introduces a conceptual shift in the assessment of brain states for purposes of monitoring and treatment. Specifically, an approach is presented herein for analyzing spatial variation in burst suppression states which could, for example, provide valuable insight into neural circuit dysfunction underlying a given pathology, as well as improve monitoring, say, of a medically-induced coma. In addition, analysis of temporal dynamics within burst epochs of a burst suppression state could help assess an underlying non-burst suppression brain state. Such approach could be explored, for example, as a prognostic tool for recovery from a coma, or for guiding treatment of status epilepticus.

In accordance with one aspect of the disclosure, a system for monitoring a subject is provided. The system includes an input configured to receive physiological feedback from locations associated with a subject's brain, and a processor configured to receive the physiological feedback from the input, assemble a set of time-series data using the received physiological feedback, and identify portions of the set of time-series data that indicate a burst suppression activity. The processor is also configured to identify, using the identified portions, locations about the subject's brain exhibiting a burst suppression state to determine a spatial pattern of the burst suppression activity, and determine, using the spatial pattern, a current and/or a future state of the brain of the patient. The system also includes a display configured to indicate the current and/or the future state of the brain of the subject.

In accordance with another aspect of the disclosure, another system for monitoring a subject is provided. The system includes an input configured to receive physiological feedback from locations associated with a subject's brain, and a processor configured to receive the physiological feedback from the input, assemble a set of time-series data using the received physiological feedback, and identify portions of the set of time-series data that indicate a burst suppression state. The processor is also configured to identify a burst characteristic profile associated with a burst pattern determined from the identified portions and compare the burst characteristic against a reference set of burst profiles. The processor is further configured to determine, based on the comparison, a likelihood of a brain state of the subject underlying the burst suppression state. The system also includes a display configured to indicate the likelihood of the determined brain state.

In accordance with another aspect of the disclosure, a method for monitoring a subject is provided. The method includes steps of receiving physiological feedback from at least one sensor configured to acquire physiological information from locations associated with a subject's brain, assembling a set of time-series data using the received physiological feedback, and identifying portions of the set of time-series data that indicate a burst suppression activity. The method also includes identifying, using the identified portions, locations about the subject's brain exhibiting a burst suppression state to determine a spatial pattern of the burst suppression activity, and determining, using the spatial pattern, a current and/or a future state of the brain of the patient. The method further includes generating a report indicating the determined current and/or future state.

In accordance with another aspect of the disclosure, a method for monitoring a subject. The method includes steps of receiving physiological feedback from at least one sensor configured to acquire physiological information from locations associated with a subject's brain, assembling a set of time-series data using the received physiological feedback, and identifying portions of the set of time-series data that indicate a burst suppression state. The method also includes identifying a burst characteristic profile associated with a burst pattern determined from the identified portions, and comparing the burst characteristic against a reference set of burst profiles. The method further includes determining, based on the comparison, a likelihood of a brain state of the subject underlying the burst suppression state, and generating a report indicative of the likelihood of the determined brain state determined.

The foregoing and other aspects and advantages of the disclosure will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 13A shows EEG voltage trace.

FIG. 13B shows segmentation of the EEG into periods of suppression, non-suppression, and periods of artifact.

FIG. 13C shows spectrogram of the EEG.

FIG. 13D shows burst suppression probability (BSP).

FIG. 13E shows temperature time series.

FIG. 13F shows representative examples of burst EEG voltage traces and

FIG. 13G shows corresponding burst spectrograms at three different temperatures.

FIG. 14A shows EEG voltage trace.

FIG. 14B shows segmentation of the EEG into periods of suppression, non-suppression, and periods of artifact.

FIG. 14C shows spectrogram of the EEG.

FIG. 14D shows burst suppression probability (BSP).

FIG. 14E shows temperature time series.

DETAILED DESCRIPTION OF THE INVENTION

Figure 1A:
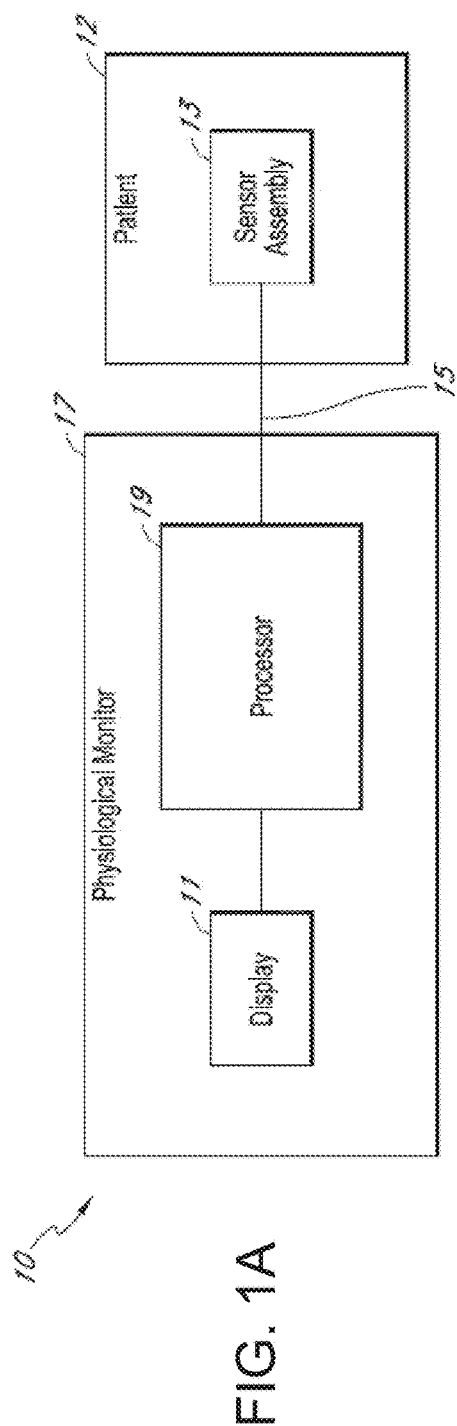
FIG. 1A-B are schematic illustrations of examples systems for monitoring a subject under in accordance with the present disclosure.
Figure 1B:
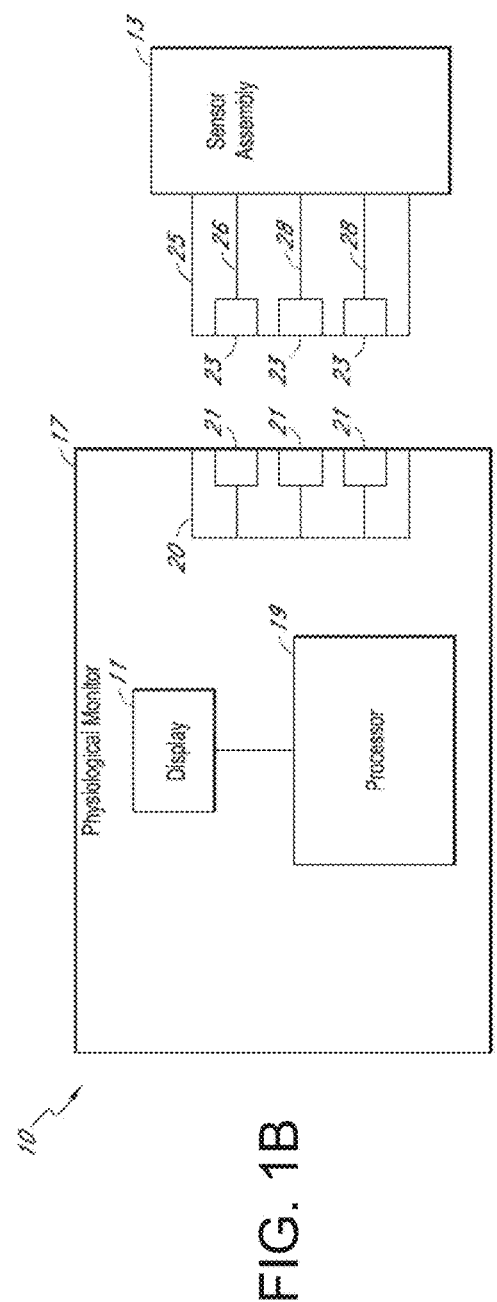

Referring specifically to the drawings, FIGS. 1A and 1B illustrate example patient monitoring systems having inputs that can be connected to sensors that can be used to provide physiological monitoring of a patient, such as brain state monitoring using measures of brain activity.

For example, FIG. 1A shows an embodiment of a physiological monitoring system 10. In the physiological monitoring system 10, a subject 12 is monitored using one or more sensors 13, each of which transmits a signal to a connection or input represented by a cable 15 to a physiological monitor 17. The physiological monitor 17 includes a processor 19 and, optionally, a display 11. The one or more sensors 13 include sensing elements such as, for example, electrical EEG sensors, or the like. The sensors 13 can generate respective signals by measuring a physiological parameter of the patient 12. The signals are then processed by one or more processors 19. The one or more processors 19 then communicate the processed signal to the display 11 if a display 11 is provided. In an embodiment, the display 11 is incorporated in the physiological monitor 17. In another embodiment, the display 11 is separate from the physiological monitor 17. The monitoring system 10 is a portable monitoring system in one configuration. In another instance, the monitoring system 10 is a pod, without a display, and is adapted to provide physiological parameter data to a display.

For clarity, a single block is used to illustrate the one or more sensors 13 shown in FIG. 1A, which may be configured for placement in proximity to, or within a subject 12 anatomy. It should be understood that the sensor 13 shown is intended to represent one or more sensors. In an embodiment, the one or more sensors 13 include a single sensor of one of the types described below. In another embodiment, the one or more sensors 13 include at least two EEG sensors. In still another embodiment, the one or more sensors 13 include at least two EEG sensors and one or more brain oxygenation sensors, and the like. In each of the foregoing embodiments, additional sensors of different types are also optionally included. Other combinations of numbers and types of sensors are also suitable for use with the physiological monitoring system 10.

In some embodiments of the system shown in FIG. 1A, all of the hardware used to receive and process signals from the sensors are housed within the same housing. In other embodiments, some of the hardware used to receive and process signals is housed within a separate housing. In addition, the physiological monitor 17 of certain embodiments includes hardware, software, or both hardware and software, whether in one housing or multiple housings, used to receive and process the signals transmitted by the sensors 13. Moreover, in other embodiments, the physiological monitor 17 can process detection of a brain state as described herein and output an indicator or generate an alarm to notify clinicians.

As shown in FIG. 1B, the EEG sensor 13 can include a connection or input, represented by a cable 25. The cable 25 can include three conductors within an electrical shielding. One conductor 26 can provide power to a physiological monitor 17, one conductor 28 can provide a ground signal to the physiological monitor 17, and one conductor 28 can transmit signals from the sensor 13 to the physiological monitor 17. For multiple sensors, one or more additional connections 15 can be provided.

In some embodiments, the ground signal is an earth ground, but in other embodiments, the ground signal is a patient ground, sometimes referred to as a patient reference, a patient reference signal, a return, or a patient return. In some embodiments, the cable 25 carries two conductors within an electrical shielding layer, and the shielding layer acts as the ground conductor. Electrical interfaces 23 in the cable 25 can enable the connection to electrically connect to electrical interfaces 21 in a connector 20 of the physiological monitor 17. In another embodiment, the sensor 13 and the physiological monitor 17 communicate wirelessly.

Figure 1C:
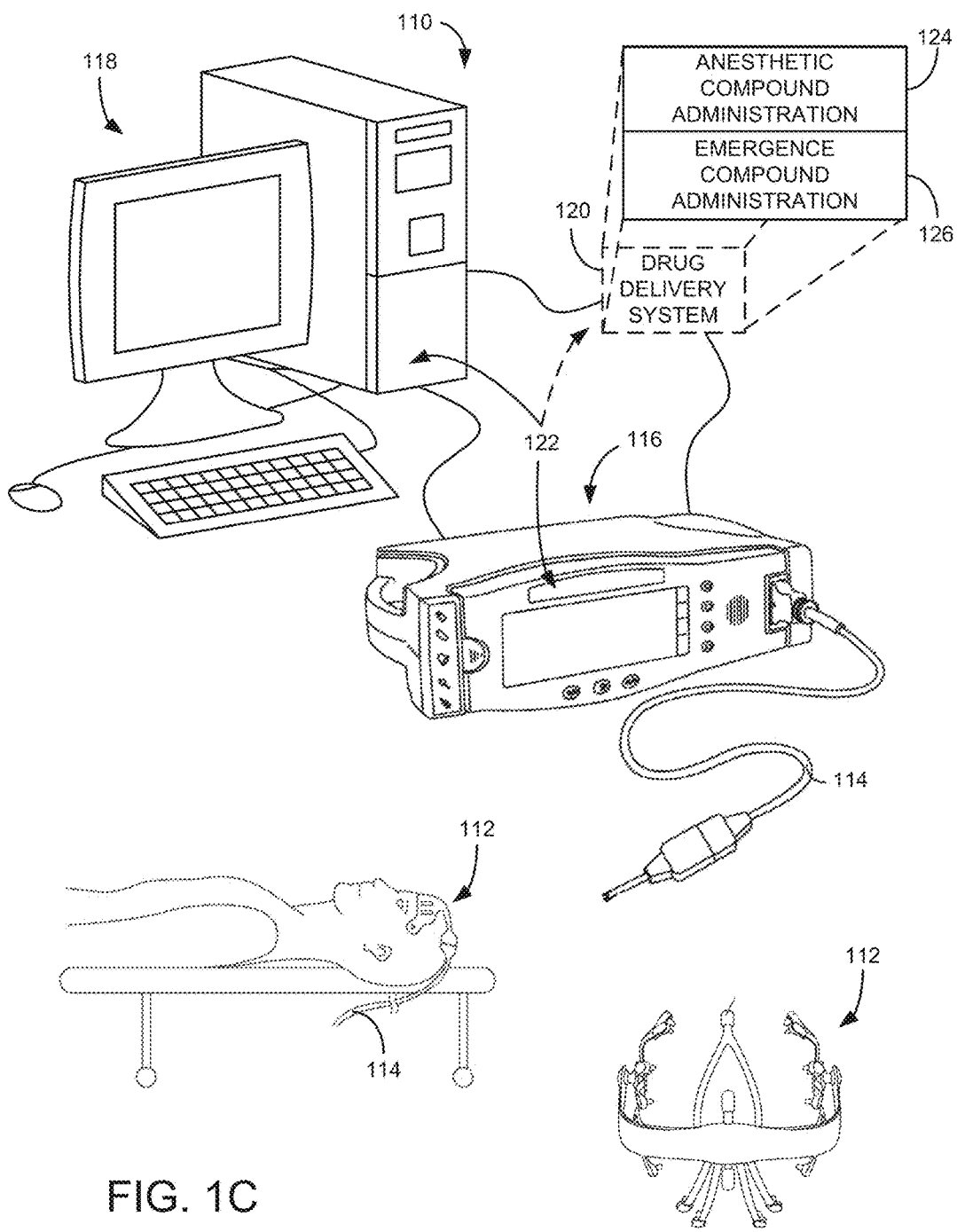
FIG. 1C is an illustration of an example system for monitoring and/or control system in accordance with the present disclosure.

Specifically referring to FIG. 1C, an example system 110 is illustrated, for use in monitoring and/or controlling a state of a patient associated with a medical condition or procedure, such as administration of an anesthetic compound or compounds, or a result of a medical condition or injury. The system 110 includes a patient monitoring device 112, such as a physiological monitoring device, a monitoring system 116, and an analysis system 118, or processor.

As illustrated in FIG. 1C, the patient monitoring device 112 may be an electroencephalography ("EEG") electrode array. However, it is contemplated that the patient monitoring device 112 may also include other elements or features, such as, mechanisms for monitoring galvanic skin response ("GSR"), for example, to measure arousal to external stimuli, or other monitoring system such as cardiovascular monitors, including electrocardiographic and blood pressure monitors, and also ocular microtremor monitors. By way of example, one specific realization of this design may utilize a frontal Laplacian EEG electrode layout with additional electrodes to measure GSR and/or ocular microtremor. Another realization of this design may incorporate a frontal array of electrodes that could be combined in post-processing to obtain any combination of electrodes found to optimally detect the target signal profiles, also with separate GSR electrodes. Another realization of this design may utilize a high-density layout sampling the entire scalp surface using between 64 to 256 sensors for the purpose of source localization, also with separate GSR electrodes.

As noted above, it is contemplated that the patient monitoring device 112 may be an EEG electrode array, for example, a 64-lead EEG electrode array. However, as will be apparent to one skilled in the art, greater spatial accuracy can be achieved by increasing the number of electrodes from 64 to 128, 256, or even higher. Similarly, the present disclosure can be implemented with substantially less electrodes.

The patient monitoring device 112 is connected via an input, such as a cable 114 to communicate with a monitoring system 116, which in some designs may be a portable system or device, and provides input of physiological data acquired from a patient to the monitoring system 116. Also, the cable 114 and similar connections can be replaced by wireless connections between components. As illustrated, the monitoring system 116 may be further connected to a dedicated analysis system 118. Also, in some designs, the monitoring system 116 and analysis system 118 may be integrated.

The monitoring system 116 may be configured to receive raw signals acquired by an EEG electrode array and assemble, and even display, the raw signals as EEG waveforms. Accordingly, the analysis system 118 may receive the EEG waveforms from the monitoring system 116, process and analyze the EEG waveforms and signatures therein based on, for instance, a selected anesthesia compound or identified condition, to determine a brain state of the patient using the analyzed EEG waveforms and signatures. In particular, the monitoring system 116 and analysis system 118 may be configured to analyze spatial and temporal characteristics describing acquired EEG data, such as, identifying and characterizing spectral features associated with burst periods, to infer an underlying physiological state. For example, the analysis system 118 may be configured to compute a burst suppression probability ("BSP") using physiological data acquired from a number of arrangements and combinations of sensors in the EEG electrode array.

The monitoring system 116 may also be configured to generate a report, for example, as a printed report or, preferably, a real-time display, indicating signature information, determined state(s) or index. However, it is also contemplated that the functions of monitoring system 116 and analysis system 118 may be combined into a common system.

In some configurations, the system 110 may also include a controller for controlling the state of a subject, such as, a drug delivery system 120. The drug delivery system 120 may be coupled to the analysis system 120 and monitoring system 116, such that the system 110 forms a closed-loop monitoring and control system. Such a closed-loop monitoring and control system in accordance with the present disclosure is capable of a wide range of operation, and may include a user interface 122, or user input, to allow a user to configure, for example, the closed-loop monitoring and control system, receive feedback from the closed-loop monitoring and control system, and, if needed reconfigure and/or override the closed-loop monitoring and control system.

The system 110 can include or be coupled to a drug delivery system 120 including any sub-systems. For example, the drug delivery system 120 may include an anesthetic compound administration system 124 that is designed to deliver doses of one or more anesthetic compounds to a subject and may also include a emergence compound administration system 126 that is designed to deliver doses of one or more compounds that will reverse general anesthesia or the enhance the natural emergence of a subject from anesthesia. In some aspects, the drug delivery system 120 is not only able to control the administration of anesthetic compounds for the purpose of placing the patient in a state of reduced consciousness influenced by the anesthetic compounds, such as general anesthesia or sedation, but can also implement and reflect systems and methods for bringing a patient to and from a state of greater or lesser consciousness.

In some aspects, systems, as described, may be configured to record EEG data, either intermittently or in real-time, identify one or more burst or burst suppression characteristics or signatures therein, and analyze the dynamics associated identified characteristics or signatures, including frequency content, waveform patterns, phase-amplitude modulation, and coherence. This information can be read out directly, or can be used to infer an underlying brain state. Inferences may include the presence of seizure activity, the effects of anesthetic drugs or other drugs that may be present, diagnostic assessments of neurological condition after brain trauma or other neurological insult, and prognostic assessments of patients in coma states, such as postanoxic coma or medically-induced coma.

In addition, provided systems may further be configured to record EEG data across multiple brain areas and analyze the spatial EEG patterns, including power, frequency, phase offsets, timing differences, and coherence differences across multiple sites. Analyses can be performed directly on scalp EEG signals or after transformation into source space. This information can be read out directly or can be used to make inferences, including depth of anesthesia, site of brain injury, site of epileptic focus, and diagnostic and prognostic assessments for patients in burst suppression due to neurological trauma or medically-induced coma. In certain configurations, such systems may combine both these spatial and temporal features to provide similar information as above.

Figure 2:
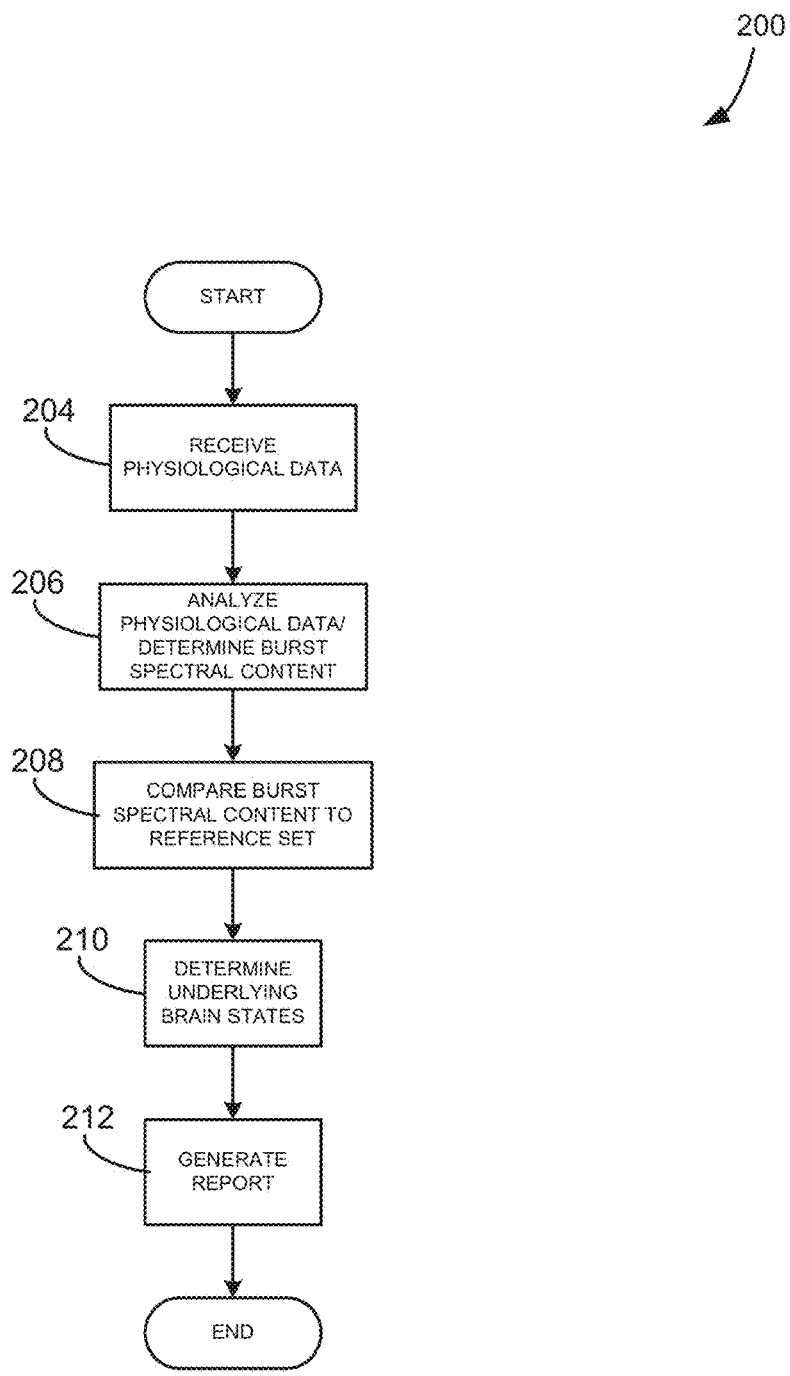
FIG. 2 is a flow chart setting forth the steps of a method for determining the state of a patient's brain during burst suppression in accordance with the present disclosure.

Referring to FIG. 2, steps of a process 200 carried out in accordance with the present disclosure are provided. The process 200 may begin at process block 204 whereby various amounts of physiological data, such as EEG data, may be received. In some aspects, at process block 204, a data acquisition step be performed using, for example, systems as described with respect to FIGS. 1A-C. In particular, acquisition may include specifying a desired drug, such as anesthesia compound or compounds, and/or a particular patient profile, such as a patient's age height, weight, gender, condition, or the like. Such selection may be communicated through a user interface, for example, as described with respect to FIG. 1C. Furthermore, drug administration information, such as timing, dose, rate, and the like, in conjunction with the above-described physiological data may be acquired and used to estimate current and predict future patient states in accordance with the present disclosure.

The following drugs are examples of drugs or anesthetic compounds that may also be used with the present disclosure: Propofol, Etomidate, Barbiturates, Thiopental, Pentobarbital, Phenobarbital, Methohexital, Benzodiazepines, Midazolam, Diazepam, Lorazepam, Dexmedetomidine, Ketamine, Sevoflurane, Isoflurane, Desflurane, Remifenanil, Fentanyl, Sufentanil, Alfentanil, and the like. However, the present disclosure recognizes that each of these drugs, induces very different characteristics or signatures, for example, within EEG data or waveforms.

Figure 3:
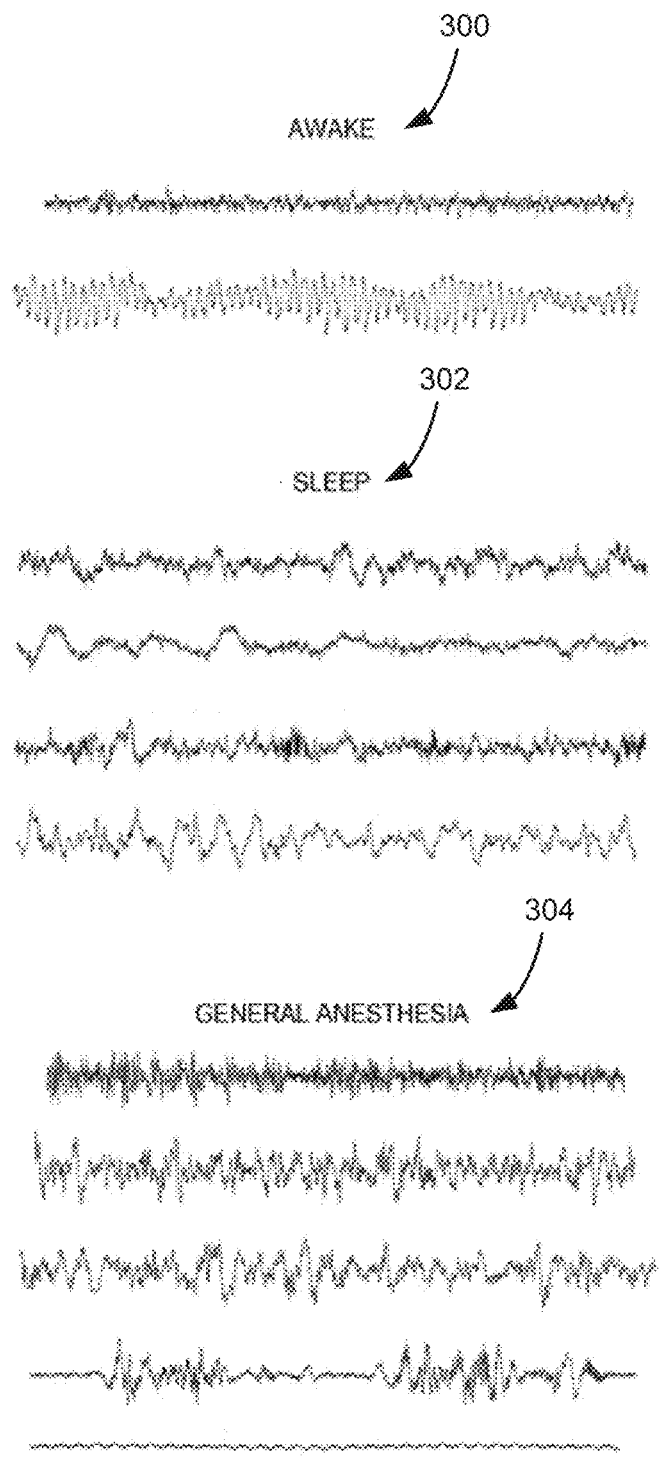
FIG. 3 is a series of electroencephalogram ("EEG") waveforms collected to illustrate variations therein that can be observed as corresponding with respective patient states.

In some aspects, a pre-processing of the acquired physiological data may be performed at process block 204, to include steps of assembling the data as time-series data, or waveforms, as well as signal filtering and/or averaging steps, for purposes of noise removal, or signal isolation, for example, using frequency-dependent methods. In addition, the raw or pre-processed physiological data may be resampled as well. Referring to FIG. 3, a series of example EEG data assembled as time domain waveforms are illustrated. As is clear in a side-by-side comparison illustrated in FIG. 3, these EEG waveforms vary appreciably. For example, general categories of "awake" 300, "asleep" 302, and under "general anesthesia" 304 can be readily created. In the side-by-side comparison with the associated category titles 300, 302, 304 indicating the state of the patient when the EEG waveform was collected, one can see that there are general, distinguishing characteristics of the EEG waveforms within each category 300, 302, 304.

However, when the time-series are not categorized or assembled with comparative waveforms that provide a context for evaluating the given data, distinguishing between or abstractly categorizing the waveforms is very difficult. Thus, as will be described, the present disclosure calls for analyzing acquired physiological data from a patient, analyzing the information and the key indicators included therein, and extrapolating information regarding a current and/or predicted future state of the patient. Specifically, the meaning of "and/or" in accordance with the present disclosure and with reference to the preceding statement as an example, should be understood as meaning the current and future state of the patient, or, either the current state or the future state. That is, the "and/or" represents the alternative options of the conjunctive "and" and the disjunctive "or," thereby covering both. In one exemplary embodiment, the current state of the patient may be indicative of the future state of the patient while not receiving general anesthesia. In other words, the current state of the patient may, for example, predict the state of the patient if burst suppression is lifted by knowing the dynamics associated with bursts while the patient is induced by general anesthesia.

Figure 4:
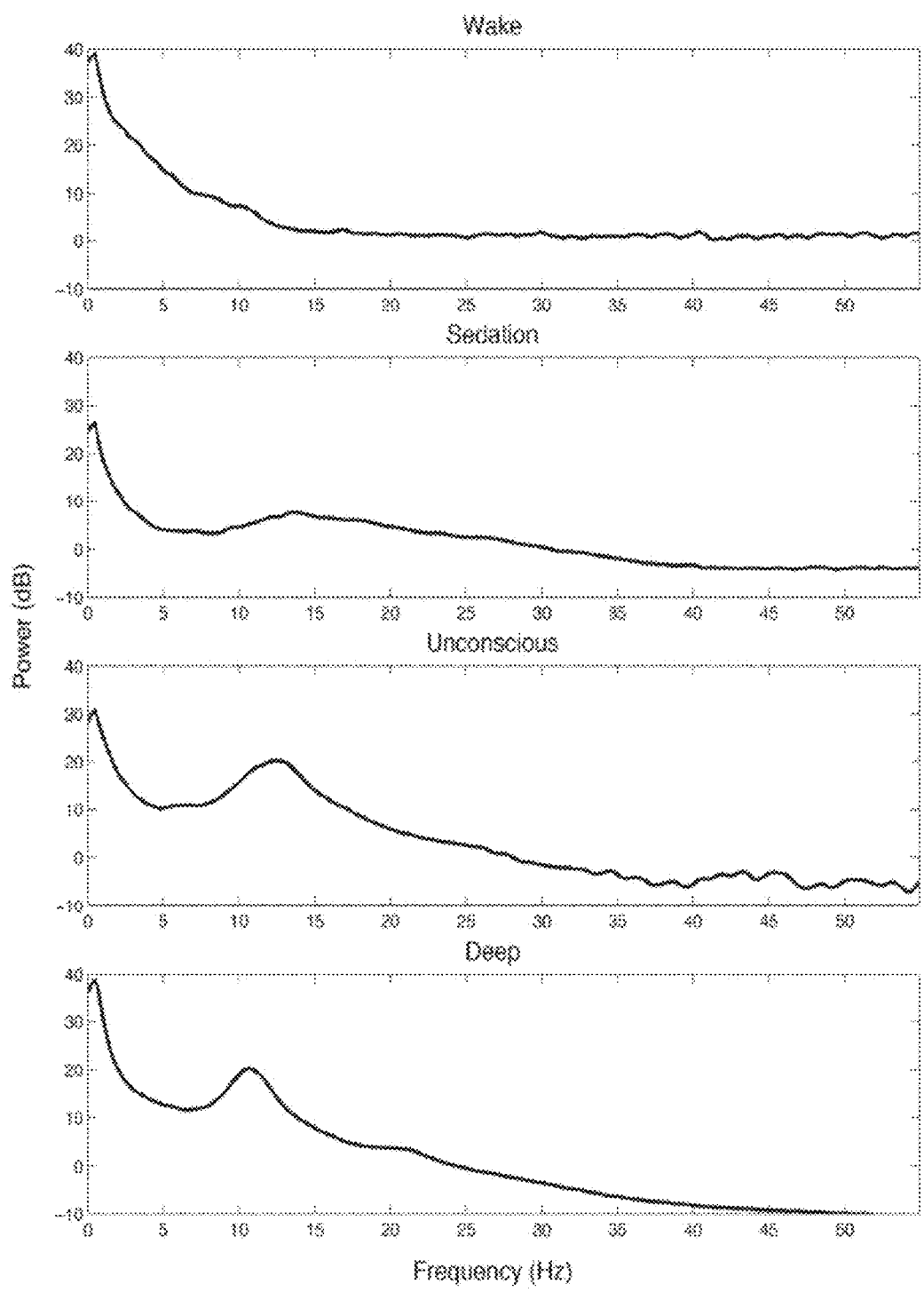
FIG. 4 is a series of graphs illustrating spectral data for one prominent drug, propofol, for use in accordance with the present disclosure.

Continuing with the process 200 of FIG. 2, at process block 206 the acquired physiological data is analyzed. As will be described, analysis at process block 206 may include a number of steps of identifying, and/or extracting features or signatures describing the data, including information related to frequency content, waveform patterns, phase-amplitude modulation, and coherence, as well as other computed quantities or indicators. For example, processed EEG data, depicting spectral signatures associated specific states resulting from administration of one prominent anesthetic drug, namely propofol, are shown in FIG. 4. In some aspects, signatures or features specific to particular episodes, or epochs identified in the data, for example, periods of burst and burst suppression, may be analyzed for purposes of determining spatial and temporal correlations, and other information. In one embodiment, burst spectral content may be determined at process block 206, and may be tracked spatially and temporally, for example to determine whether spectral content of bursts have returned to a pre-burst suppression state, or whether a frequency feature has changed over time.

Figure 5B:
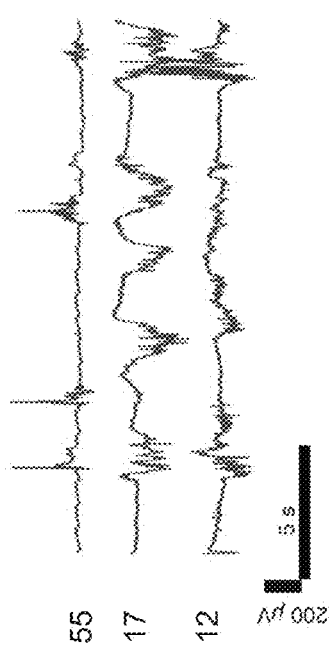
FIG. 5B is a series of EEG time-series data acquired from different cortical regions exhibiting asynchronous burst suppression.
Figure 5C:
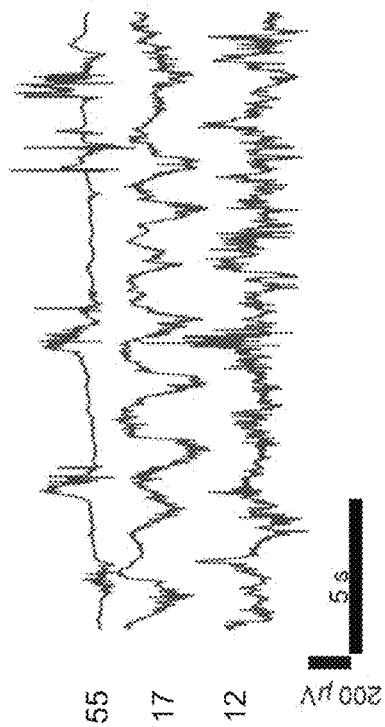
FIG. 5C is the series of EEG time-series data of FIG. 5B where one channel is in burst suppression and the remaining channels are not in burst suppression.
Figure 5A:
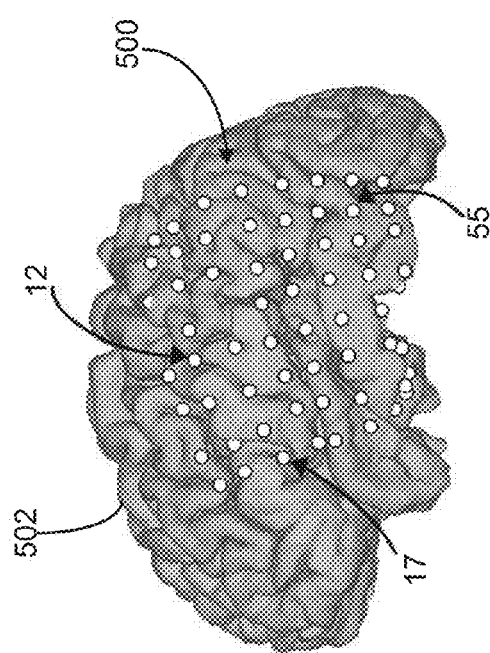
FIG. 5A is an illustration of a reconstructed magnetic resonance ("MR") image of a brain depicting grid electrode locations.

By way of example, intracranial electrocorticograms were recorded from a subject exhibiting burst and burst suppression activity while undergoing general anesthesia. As illustrated in FIG. 5A, a subdural grid of electrodes 500 broadly distributed across a subject's cortex 502, enable examination of both spatial dynamics of burst suppression within local cortical regions and larger-scale network interactions. For instance, the subdural grid of electrodes 500 can be spaced 1 cm apart and spanning up to 11 cm of cortex 502, although other electrode separations may be possible. Waveform EEG data obtained at different recording time from grid channels 12, 17, and 55 shown in FIG. 5A are illustrated in FIGS. 5B and 5C, respectively. Due to the broad spatial sampling, burst suppression pattern was found to be localized, with bursts being substantially asynchronous across the cortex.

Figure 5D:
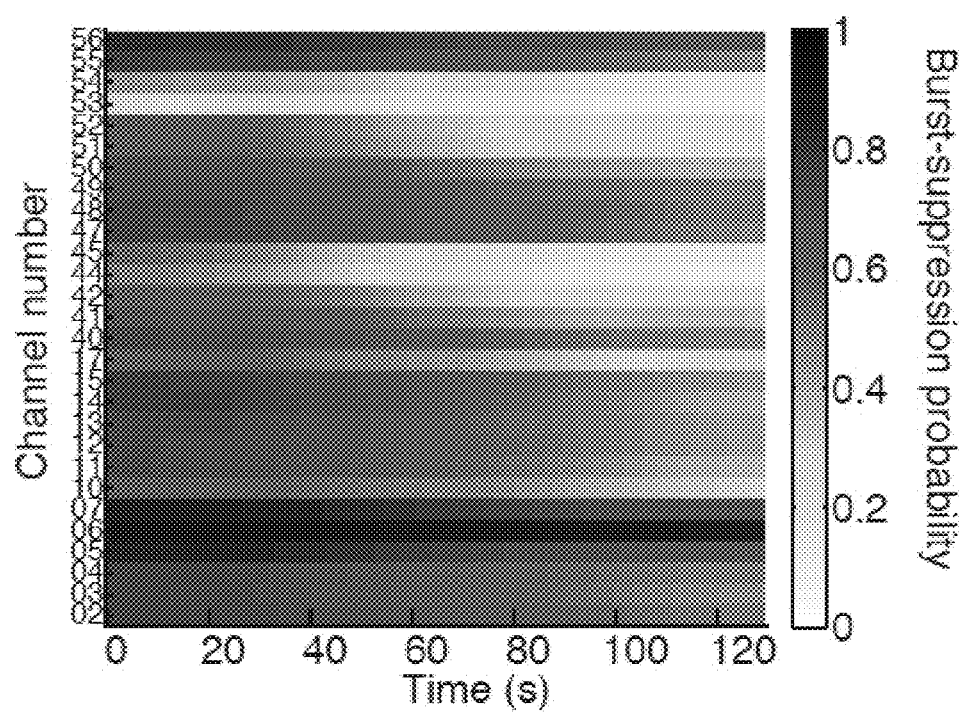
FIG. 5D is a graph illustrating the burst suppression probability ("BSP") changing over time for the channels of FIG. 5A.
Figure 5E:
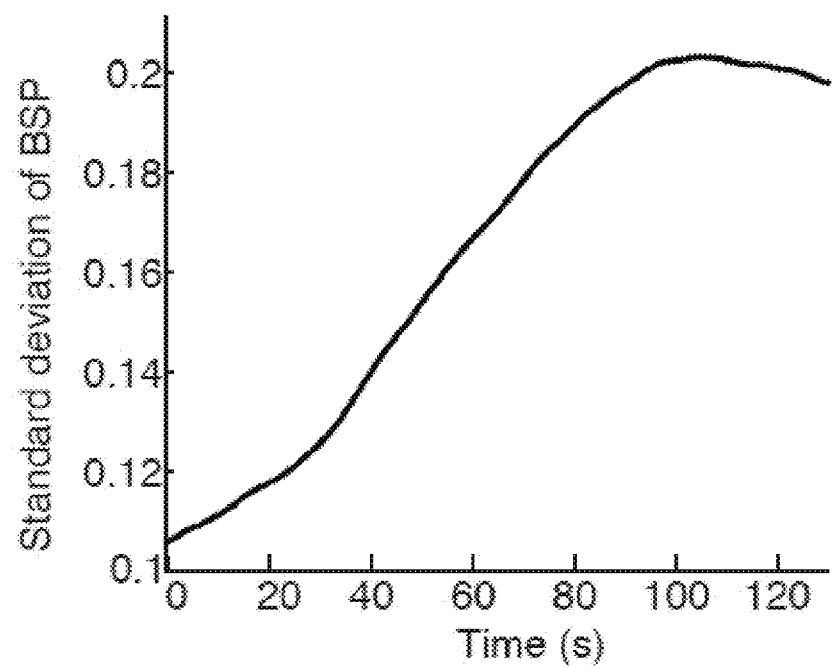
FIG. 5E is a graph illustrating the standard deviation of the BSP across all channels from FIG. 5B.

Referring now to FIG. 5D, a graphical example depicting time-variation of burst suppression probabilities is shown. Specifically, a burst suppression probability ("BSP") can be calculated from time-series data obtained using any channels from a grid of electrodes 500, as shown in FIG. 5A, whose values ranging from 0 to 1 and indicate the probability of a suppression period at a given point in time. For example, a BSP may be computed using a state-space model approach. With reference to FIG. 5D, most channels exhibit high BSP that can change appreciably over time. Specifically, a subset of channels exit burst suppression (e.g., Channel 44), while other channels maintain high BSPs (e.g. channel 5 remains in burst suppression with a BSP above 0.5). The standard deviation of the BSP across the recording sites may range from 0.04 to as high as 0.2, for example, as shown in FIG. 5E. The increasing standard deviation demonstrates that the BSPs in different cortical regions are becoming uncoupled as they diverge into different states. The mean range of the BSP across the grid of electrodes 500 at a given point in time is approximately 0.46, demonstrating a large average difference in burst dynamics across channels. These measures indicate that burst suppression dynamics can often diverge substantially across different cortical areas, with different cortical regions exhibiting different propensities for suppression.

Given that the burst suppression probability can vary widely across cortex, the state of burst suppression itself may also be restricted particular cortical regions. Thus, it may be advantageous to determine indications regarding whether a state of burst suppression is limited to any particular cortical region. Specifically, periods when any subset of channels exit burst suppression may identified using the raw or processed time-series data. For instance, periods when any particular channel does not undergo a suppression over a time interval of say, 30 seconds, may be defined as having exited burst suppression, although other values are possible. By way of example, FIG. 5B shows time-series data from different cortical regions measured with channels 12, 17, and 55 described in FIG. 5A, where all exhibit burst suppression, but with bursts being asynchronous for the respective regions. An example from a later recording using the same configuration is shown in FIG. 5C. Specifically, channel 55 exhibits burst suppression, while channels 12 and 17 do not. Hence, the state of burst suppression is not necessarily cortex-wide.

As illustrated in FIGS. 5B and 5C, a subset of channels may exit burst suppression while others remain in deep burst suppression, with BSPs over approximately 0.5. The amount of time spent in spatially isolated burst suppression may also be quantified by identifying the total time that some channels were deeply suppressed, while other channels remained nearly continuous. Epochs of deep suppression can be defined, for example, as those where any 3 channels include BSP values over 0.5. In the example shown in FIGS. 5A-5E, amounting to 15.9 minutes in duration, 4.6 minutes (28.7%) include at least 3 other channels that have a BSP less than 0.2, that is, at least 3 channels that remained in a lighter state of suppression.

As a result, one region of a subject's cortex can be in a state of burst suppression, while neighboring cortical regions exhibit continuous activity characteristic of a lighter stage of anesthesia. Burst suppression can therefore occur in limited cortical regions, and does not necessarily reflect a cortex-wide phenomenon. In addition, complex temporal structure within bursts can be present, that recapitulate the spectral dynamics of the state preceding burst suppression, and evolve throughout the course of a single burst.

As previously discussed, spatially isolated burst dynamics can occur even when an entirety of a subject's cortex is in burst suppression. The spatial distribution of individual bursts may be examined in order to test whether bursts are sometimes constrained to a limited cortical region, as suggested by FIG. 5B. Each burst can be individually analyzed and identified to determine which grid channels participated in the burst by selecting those with nearby burst onset times.

Figure 6A:
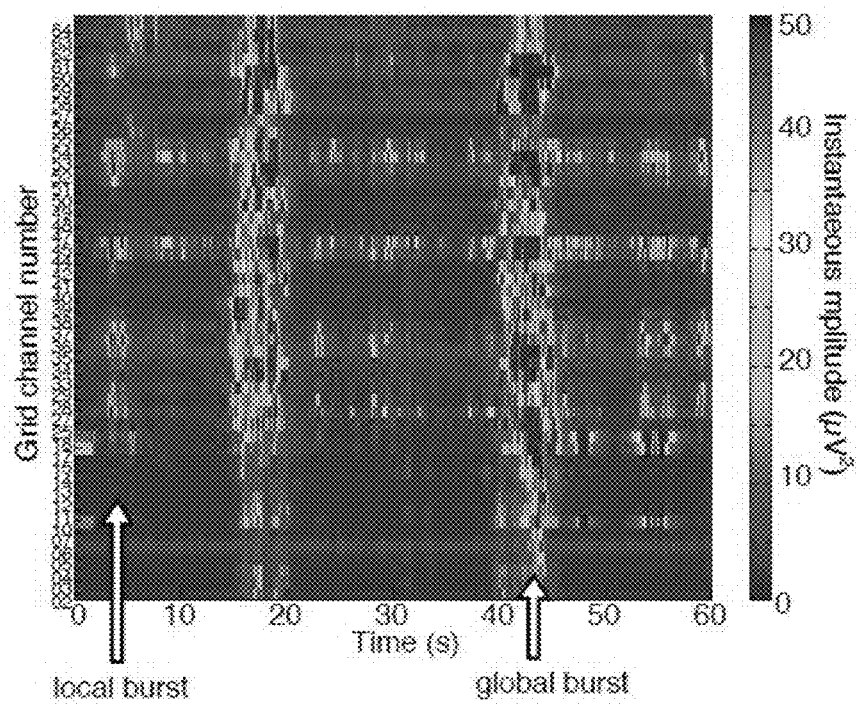
FIG. 6A is a graph illustrating the instantaneous amplitude across the grid channels over time.

Continuing with aspects of analysis at process block 206 of FIG. 2, an instantaneous amplitude describing the physiological data may be compared across multiple locations of a subject's anatomy. As illustrated in the example of FIG. 6A, burst periods can change as a function of location and time. For example, a burst at t=42 seconds involves all channels measured, but the burst at t=5 seconds occurs in only a small subset of electrodes, indicating that a limited cortical region is bursting. In the example of FIG. 6A, bursts were observed in only a subset of the grid channels while other regions remained suppressed. These local bursts were interspersed with global bursts that occurred across all channels, demonstrating that the state of burst suppression was present across cortex but that individual bursts could occur asynchronously.

Figure 6B:
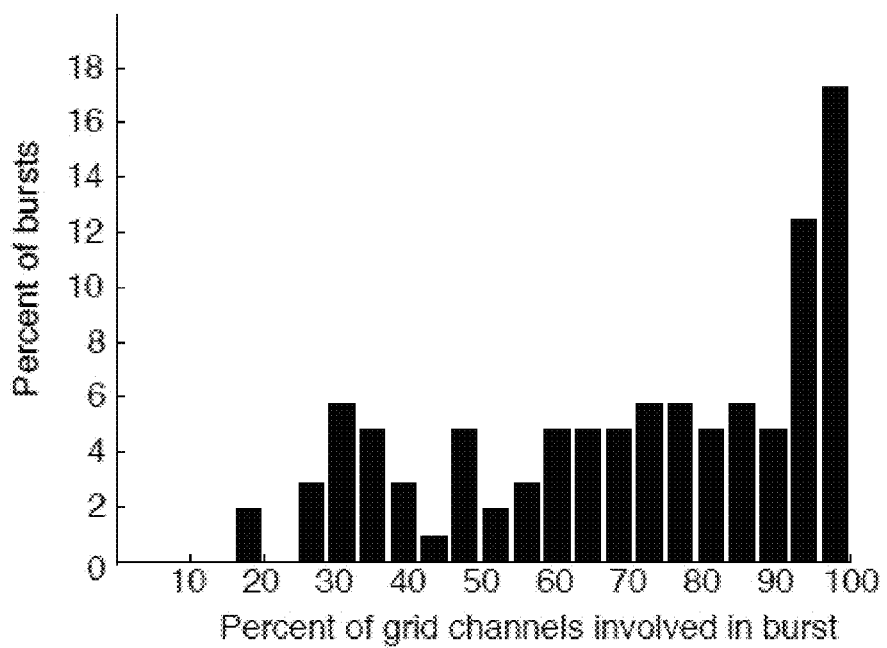
FIG. 6B is a histogram illustrating the distribution of local and global bursts across the grid channels.

As another example, FIG. 6B illustrates a histogram showing the number of grid channels participating in each burst using data acquired from several subjects. The median percentage of channels involved in a single burst is approximately 76% (quartiles: 52%-94%), demonstrating that local bursts made up a substantial portion of total bursting, as indicated by the long leftward tail to the distribution. As a result, bursts can be either global or local, and local bursts may reflect activation in a limited cortical area while other regions continue to be suppressed. In addition, suppressions can continue in one region despite high-amplitude bursts in a neighboring region, suggesting that a profoundly inactivated state can be confined to specific cortical regions.

Despite the presence of spatially localized bursts, it is also clear that many bursts occur broadly across a subject's cortex, as nearly a third of bursts (31%) occurred in over 90% of channels, as shown in the example of FIG. 6B. It can therefore be tested whether these 'global' bursts across multiple channels begin simultaneously in each channel, or whether there are consistent time lags between distant channels. This may be accomplished by comparing burst onset times between any pair of electrodes, such that the mean differences in burst onset time are significantly correlated with the distance between pairs of channels.

Figure 7A:
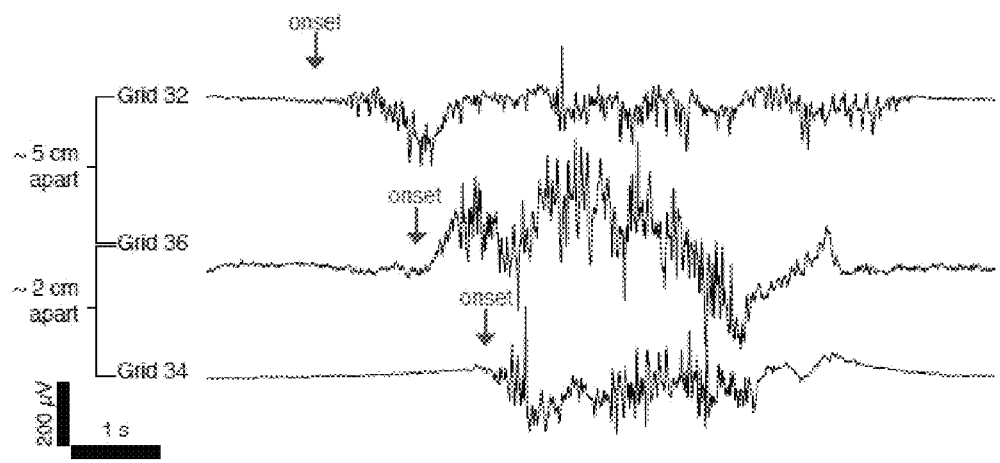
FIG. 7A is a series of EEG waveforms demonstrating a locally differentiated single global burst beginning hundreds of milliseconds apart in different cortical regions.

Continuing further with analysis at process block 206 of FIG. 2, a timing of burst onsets across multiple locations of a subject's cortex may be identified. As illustrated in the example of FIG. 7A, onset time differences may be larger between more distant pairs of channels, for instance, increasing from 225±83 ms (mean±s.d.) in adjacent (1 cm) channels to 368±107 ms (mean±s.d.) in channels separated by more than 4 cm (difference=143 ms, $p<10^{-5}$) in FIG. 7A. Because the difference in burst times is correlated with distance (R=0.30, $p<10^{-5}$), these timing differences cannot be attributed simply to noise in the automated segmentation algorithm; even if the entire difference between adjacent channels was due to segmentation noise, an additional 143 ms would remain as the mean difference in burst timing between distant channels. To further ensure that these results are not an artifact of the burst detection algorithm, the analysis can be repeated using the variance of the raw signal to detect burst onsets, as will be described below. Results, as shown in FIG. 7A, therefore demonstrate that even a single 'global' burst can be locally differentiated, and can begin hundreds of milliseconds apart in different cortical regions, as illustrated by channel 32, that starts hundreds of milliseconds before the bursts in channels 36 and 24.

Figure 7B:
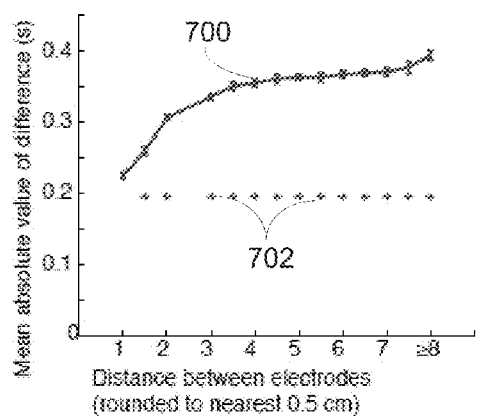
FIG. 7B is a graph illustrating the mean difference in burst onset times between pairs electrodes.
Figure 7C:
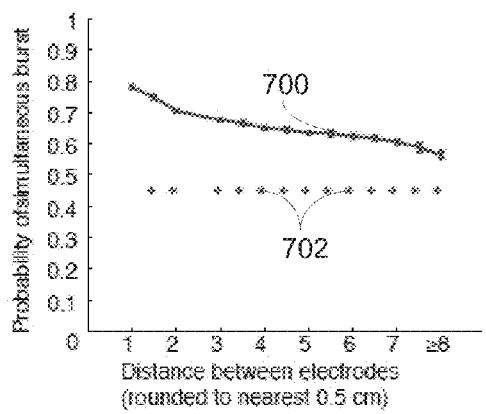
FIG. 7C is a graph illustrating the probability of joint bursts between pairs of electrodes.

By way of example, a plot of difference in burst onset times between pairs of electrodes is shown in FIG. 7B, illustrating substantial timing differences in burst onsets between distant electrodes, with distant electrodes showing larger gaps in burst timing. Specifically, the top line 700 represents the mean and standard error of the difference in burst onset times, and the bottom stars 702 mark distances that are significantly different than pairs 1 cm apart. In addition, FIG. 7C shows that spatial heterogeneity can be further tested, for example, by computing the probability that two different electrodes are simultaneously in a bursting state. As illustrated in the example FIG. 7C, adjacent electrodes had a 78.1% probability of being in a burst state simultaneously, whereas more distant electrodes shared only a 62.0% chance of simultaneous bursting ($p<10^{-5}$). Similar to results from the differences in burst timing of FIG. 7B, this demonstrates that burst onsets are asynchronous across cortex, with significant lags between distant cortical regions participating in a simultaneous burst. In addition, the probability decreases with distance, demonstrating that distant electrodes are less likely to be simultaneously in a burst state.

Figure 8:
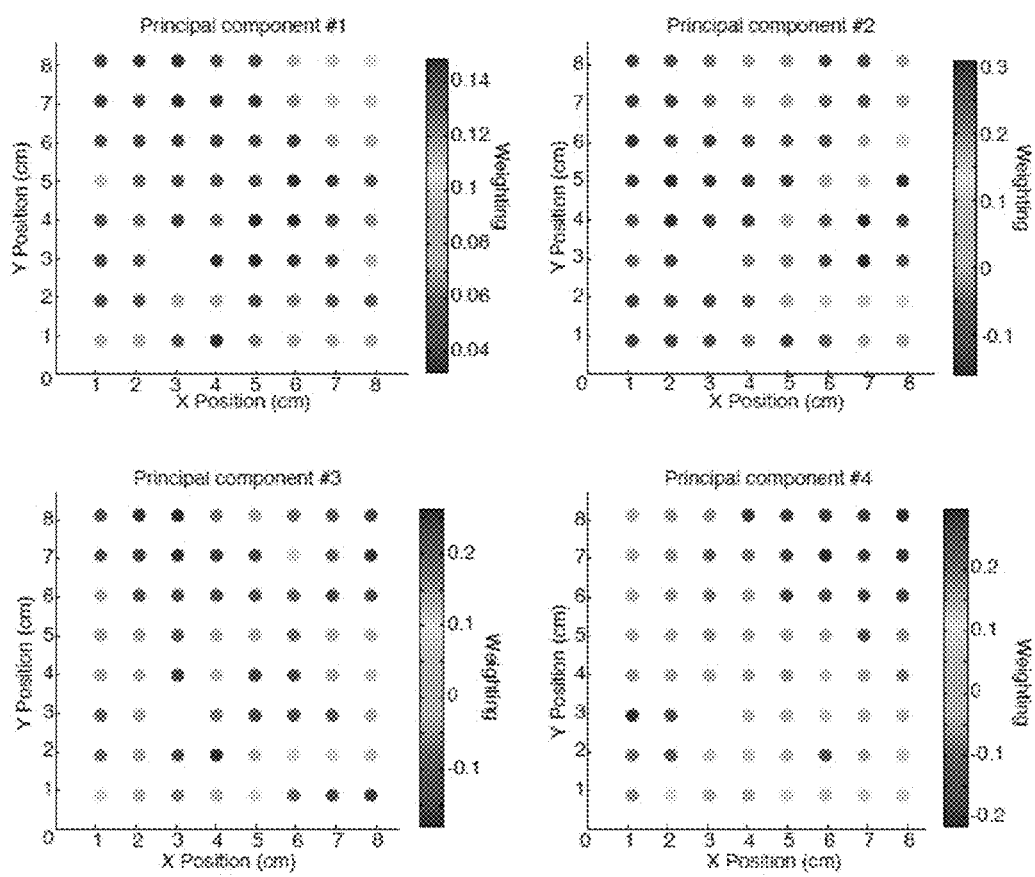
FIG. 8 is a series of graphs illustrating the color variation across the grid electrodes that shows how BSP is locally differentiated.

Taken together, above-described results demonstrate that there can be substantial heterogeneity in bursting dynamics across the cortex, and suggest that bursts are spatially clustered. To explicitly test for spatial clustering of bursts, a principal components analysis can be performed, for example, on the burst state across multiple grid electrodes. By way of example, each panel of FIG. 8 shows one of the first four principal components from a patient, whereby a color variation across the grid indicates how burst probability is locally differentiated. As may be appreciated from the example of FIG. 8, each of the components was found to be significantly spatially clustered (p<0.05), demonstrating that burst properties are anatomically clustered and differ in distant cortical regions. Further, it was determined that 78% of the variance could be explained by the first 4 components of multiple patients (not shown). Specifically, to test whether spatial clustering was present in these first 4 principal components the spatial derivative of the estimated components was compared to a randomly shuffled grid. This shuffling analysis demonstrated that 15 out of the 16 components were significantly spatially clustered (p<0.05), indicating that clusters of anatomically close cortical areas tended to share burst properties. Therefore, although burst suppression was sufficiently correlated across a cortex to produce a seemingly synchronous pattern in scalp EEG recordings, the underlying dynamics exhibited substantial local heterogeneity.

The previously discussed spatially differentiated dynamics may suggest, for example, that bursts and suppressions depend on local cortical state. This finding may be compatible with a previously described model for the generation of burst suppression, that proposes a depressed cerebral metabolism could lead to burst suppression by producing a slow cycle in ATP levels. This model makes specific predictions about the spectral content within individual bursts: first, that they can recover the dynamics of the state immediately preceding burst suppression, and second, that the recovered oscillatory features will decelerate through the course of each burst.

Figure 9:
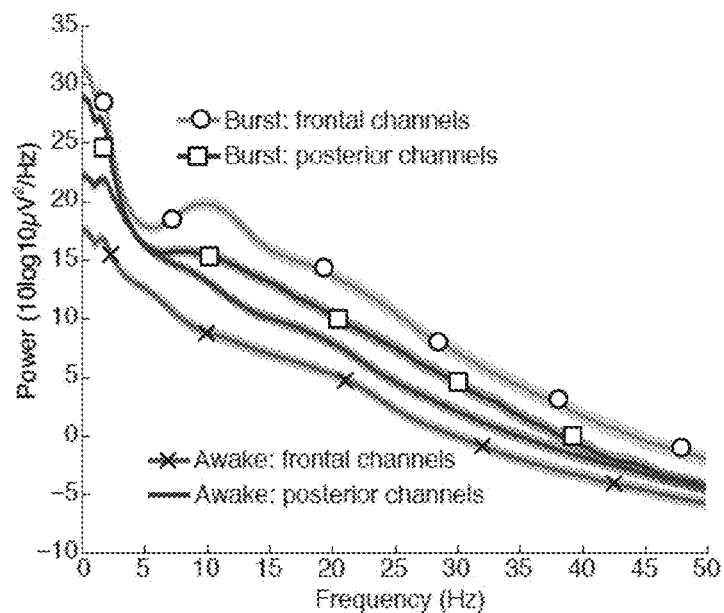
FIG. 9 is a graph illustrating the average spectra within a burst across all channels categorized by anatomical location.

As a result, at process block 206 of FIG. 2, a burst spectral content may also be determined, for example, for use in identifying whether a spectral content of bursts returned to the pre-burst suppression state, such as lighter stage of general anesthesia. For instance, general anesthesia using profol produces two striking features in an EEG: a large increase in low frequency (e.g., 0.1-4 Hz) power, and an alpha (e.g., ~10 Hz) rhythm that occurs predominantly in frontal cortex regions. As such, a within-burst spectrum across multiple channels may be computed, for example, to test whether these features were present. In certain scenarios, electrocorticography ("ECoG") channels may be used, and classified as 'frontal' if it is anterior to the central sulcus, as defined by visual inspection of, say, reconstructed MRI images, and 'posterior' otherwise. Spectra may then calculated, for example, using data from two seconds following burst onset, and averaged separately for frontal and posterior channels. By way of example, FIG. 9 shows spectral dynamics propofol-induced general anesthesia. As shown, posterior channels had a strong power component at slow frequencies, and frontal channels had both increased slow power as well as a pronounced alpha oscillation, which displays the average spectra (+/−std. err.) within a burst across all channels, categorized by anatomical location. In other words, the plot of FIG. 9 shows that the bursts contain increased slow power relative to the awake state, and a frontal alpha oscillation.

Figure 10:
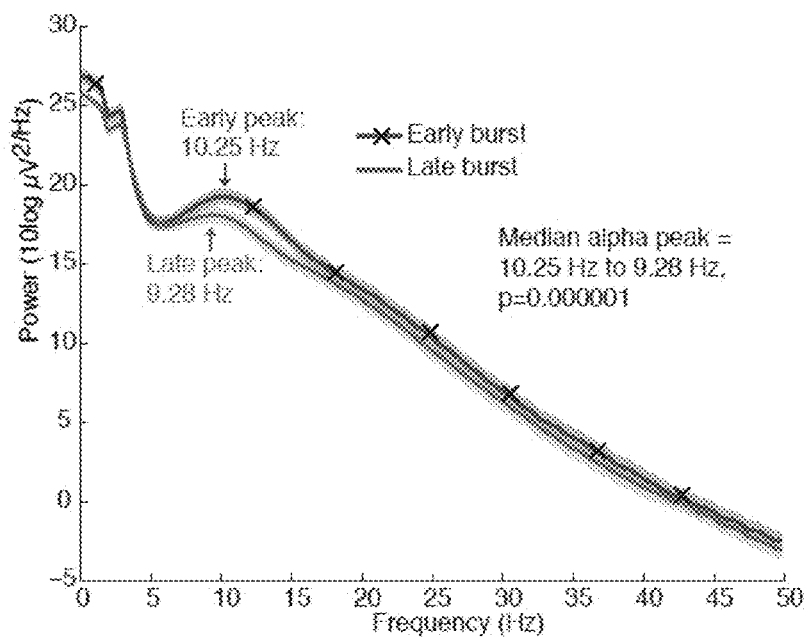
FIG. 10 is a graph illustrating the average spectra across all channels with an alpha oscillation showing there is a decrease in peak frequency between early and late portions of the burst.

As mentioned, analysis of acquired physiological data at process block 206 of FIG. 2 may also include tracking individual spectral features present. For example, given that the propofol-induced alpha rhythm was shown to resume during bursts, as shown in FIG. 10, it was investigated whether its frequency decelerated throughout a burst by first selecting all channels with a peak in power in the alpha band, defined as higher power in the alpha (e.g., 8-14 Hz) band than in the theta (e.g., 4-7 Hz) band. The time course of alpha dynamics was examined by comparing the early (e.g., 0-1.5 s) and late (e.g., 1.5-3 s) components of bursts, restricting the analysis to bursts lasting at least 3 seconds. Specifically, the spectra showed that alpha rhythms can decelerate throughout a burst, with a peak frequency dropping from approximately 10.25 Hz in the early period to approximately 9.28 Hz in the late period of the burst ($p<10^{-5}$), as illustrated in FIG. 10, which shows a significant decrease in peak frequency between the early and late components of bursts. As such, burst dynamics are therefore not only variable across cortex, but also exhibit consistent patterns within a single burst, and these patterns align precisely with the predictions of the metabolism-based model.

Figure 11:
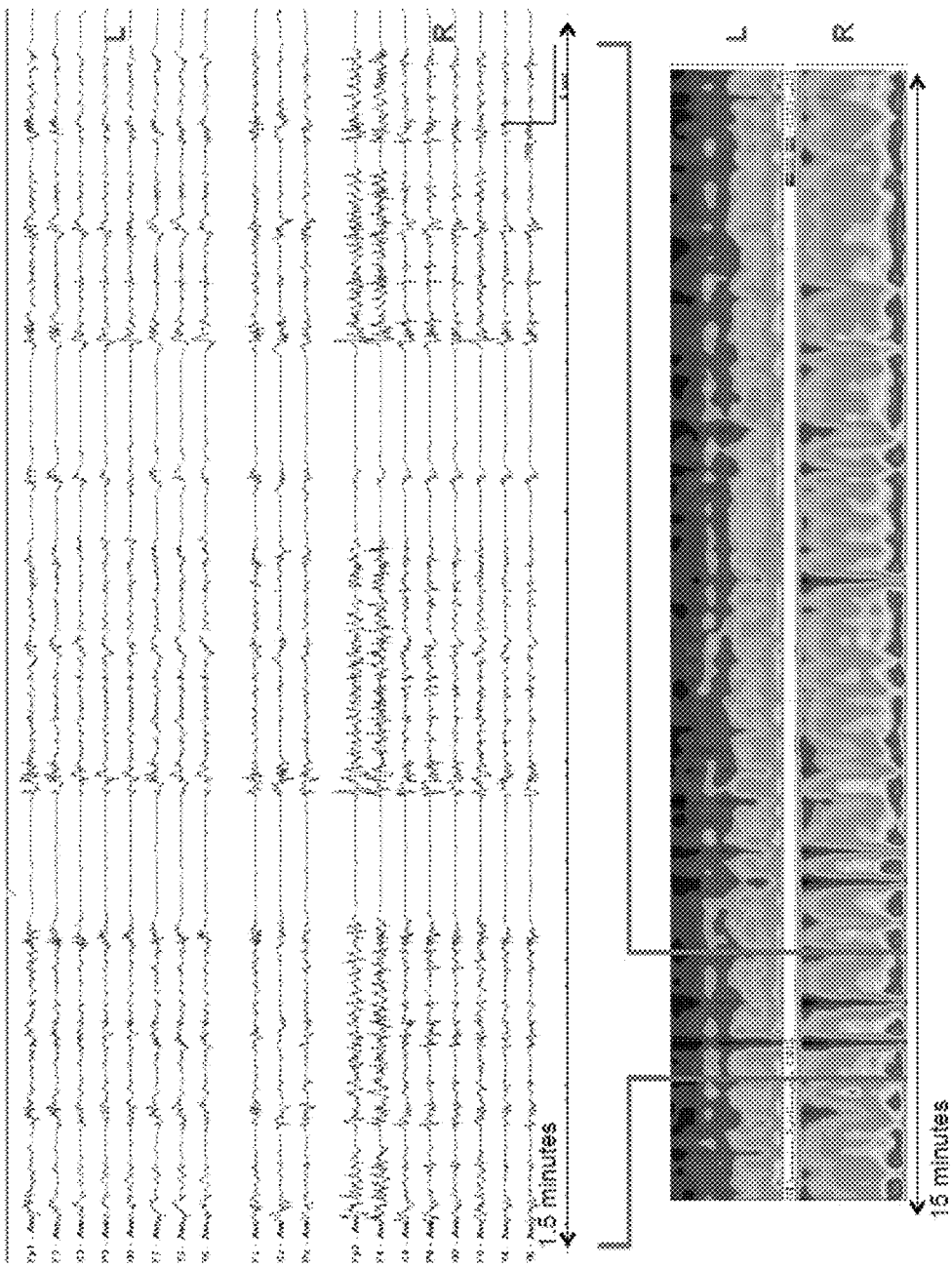
FIG. 11 is a series of scalp EEG recordings in an epilepsy patient showing that within-burst dynamics are heterogeneous across the scalp, with substantially higher power in electrodes on the right side of the brain.

Additionally, another example shown in FIG. 11, depicts scalp EEG recordings obtained from an epilepsy patient illustrating that within-burst dynamics are heterogeneous across the scalp, with substantially higher power in electrodes on the right side of the brain. This asymmetry indicates that spatial differences in burst suppression can be detected in the scalp EEG, and that there is useful clinical information (in this case, lateralization) contained within a given burst.

Figure 12A:
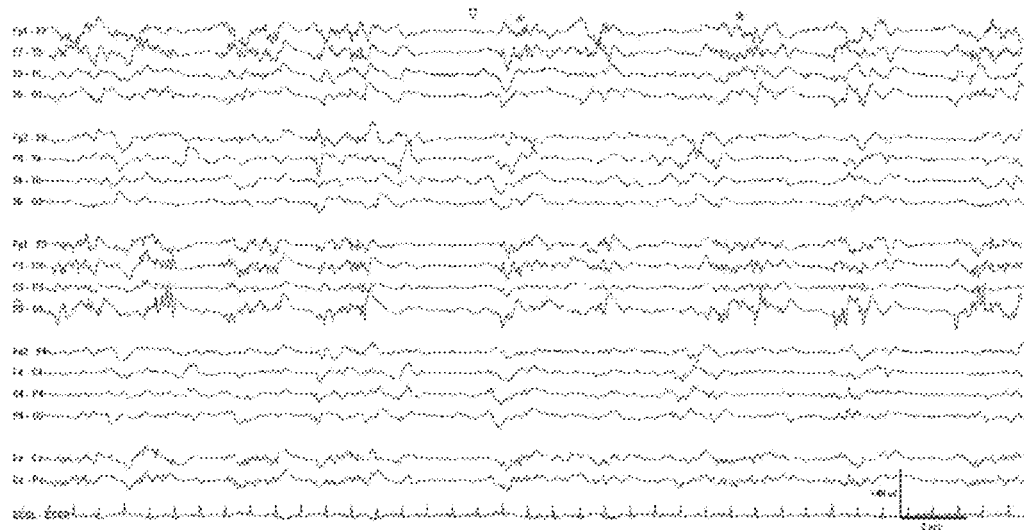
FIG. 12A is the series of scalp EEG recordings of FIG. 11 during propofol treatment showing light burst suppression and epileptiform activity.
Figure 12B:
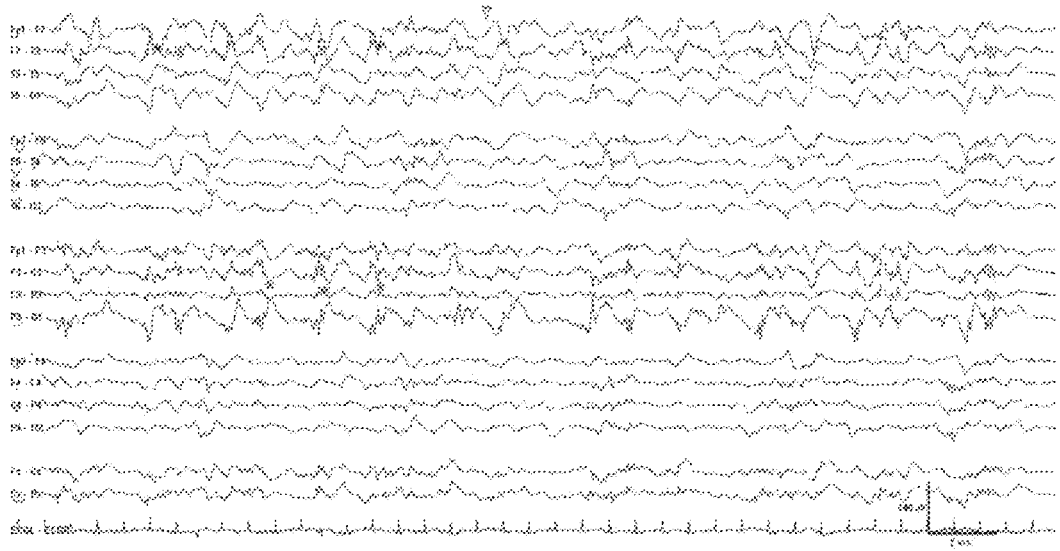
FIG. 12B is the series of scalp EEG recordings of FIG. 11 showing a long burst with epileptiform discharges in the burst.
Figure 12C:
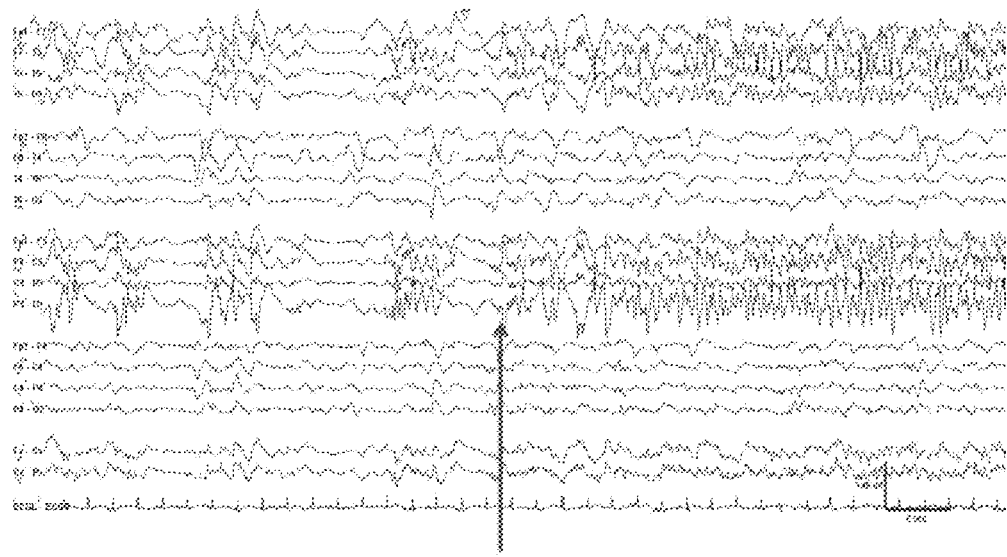
FIG. 12C is the series of scalp EEG recordings of FIG. 11 showing a seizure emerging where left sided epileptiform discharges were seen previously.
Figure 12D:
FIG. 12D is the series of scalp EEG recordings of FIG. 11 showing the end of the seizure of FIG. 12C.
Figure 12E:
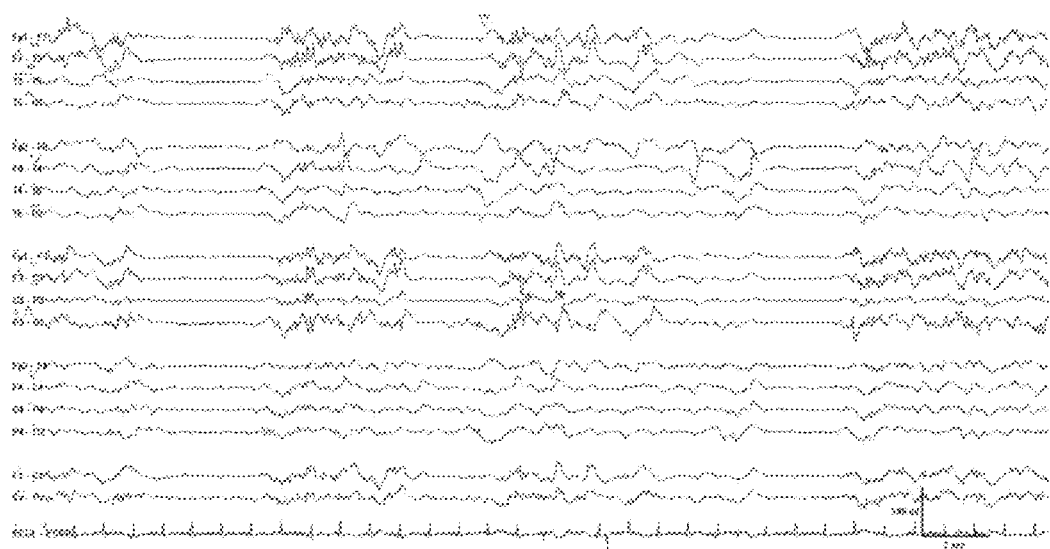
FIG. 12E is the series of scalp EEG recordings of FIG. 11 showing burst suppression with bursts containing epileptiform activity.

In another example, as shown in FIGS. 12A through 12E, multiple panels show evolution of the scalp EEG recordings in a patient undergoing propofol treatment to suppress seizures. Initially, the within-burst dynamics show signatures of epileptiform activity, suggesting that the underlying brain state if burst suppression were absent would be a seizure, as shown in FIGS. 12A and 12B. The epileptiform signatures are spatially localized to the left side, as indicated by stars. A seizure then evolves, as indicated by the arrow shown in FIG. 12C, emerging in the same spatial location as the initial epileptiform activity was observed in FIGS. 12A and 12B. This finding shows that the within-burst dynamics can identify underlying brain state (in this case, epileptiform activity), and that their spatial pattern can be used to predict the brain regions that are involved (in this case, the epileptogenic zone). FIG. 12D shows that the seizure has ended, as indicated by the arrow, and FIG. 12E shows burst suppression, as indicated by the stars, after the seizure has ended, with bursts still containing epileptiform activity.

Referring again to FIG. 2, at process block 208, determined burst spectral content, as described, may be compared to a reference set, for example, retrieved from a memory, database or storage location. In particular, the reference set could be generated using data acquired in a variety of scenarios or clinical circumstances. Specifically, such reference set could be generated using data acquired from relatively brief time periods, say, on the order of tens of seconds to minutes, for example, during intraoperative monitoring, as well as data acquired over several minutes to hours, for example, for coma or epilepsy patients in the intensive care unit. Larger databases of burst suppression reference data, or analyses that extract the essential features of such a database, could be used to predict outcomes or suggest therapies for patients in burst suppression due to coma, or in patients placed in a state of burst suppression to treat epileptic seizures. In cases where the spatial variations of burst suppression are relevant, an appropriate measurement using multiple electrode arrangements (e.g., 19 channels according to the International 10/20 system, 32 channels, 64 channels, and so on.) could be made to generate the reference data. Comparisons at process block 208 between a reference set, generated as described, and spectral content at a time interval of interest could be made using any number of standard methods, including visual inspection, statistical comparisons of spectra using jackknife, bootstrap, or F-test approaches, comparisons based on parametric forms of the spectrum, time-domain feature detection methods, linear regression, or cross-correlation methods, for instance.

Figures 14F, 14G:
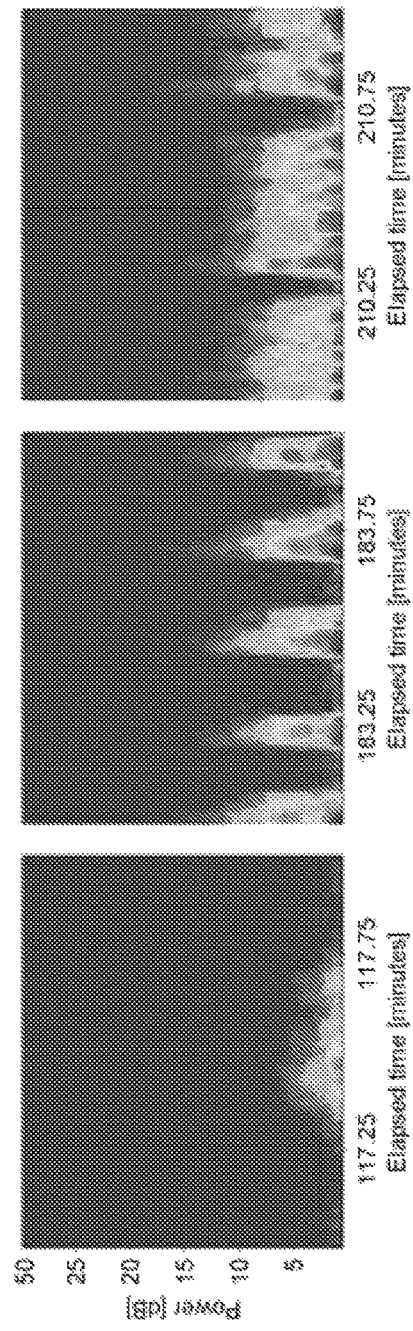
FIG. 14F shows representative examples of burst EEG voltage traces.
FIG. 14G shows corresponding burst spectrograms at three different temperatures.

By way of example, patients undergoing cardiac arrest for cardiac surgery are sometimes placed in a state of hypothermia-induced burst suppression and isoelectricity to reduce brain metabolism. Recent studies suggest that the size of bursts during burst suppression correlate with the degree of brain cooling, and thus metabolic activity, as illustrated in FIG. 13 and FIG. 14, specifically FIGS. 13F, 13G, 14F and 14G. FIGS. 13A-G show example EEG data during burst suppression induced by deep hypothermia for a representative patient and FIGS. 14A-G show example EEG data during burst suppression induced by deep hypothermia for another representative patient. Hence, reference data could be obtained prior to cooling (FIGS. 13C and 14C, left side), during the first instance of burst suppression (FIGS. 13F and 13G, left side), and at the target level of cooling (FIGS. 13F and 13G, middle panel; FIGS. 14F and 14G, left side) to establish the patient's brain states during these intervals. Burst dynamics could be characterized in a variety of ways, including spectral analysis (FIG. 11, FIG. 9, FIG. 10), as well as time domain analyses of when bursts are happening across different channels (FIG. 5B, 5C, 5D, 6A), plotted spatially against a reference brain or scalp surface (FIG. 5A, FIG. 8). During ongoing EEG monitoring, the real-time EEG could be compared, automatically or as needed, to the reference data to help ensure that the correct state is being maintained, to detect transient increases in metabolism, or to determine if the patient is not recovering brain activity adequately during the warming phase of the procedure. This information would then prompt appropriate clinical intervention that could include, for instance, measures to aid the warming or cooling process.

Referring again to FIG. 2, at process block 210, information, including burst spectral dynamics, determined using analysis steps, in accordance with the present disclosure, may be used to identify underlying states of a subject. For instance, determined spectral content within burst periods could reveal neural dynamics that remain intact when not interrupted by suppression epochs, while a shift in the spectral content of bursts may signal an opportunity to lift a pharmacologically induced coma. In some aspects, a likelihood of a given brain state underlying a burst suppression pattern may also determined.

Finally, at process block 212, a report of any shape or form may be generated, for example, as a printed report of, preferably, a real-time display of signature information and determined present and or future brain states. Specifically, a visual representation, indication, metric or index, can be provided to a clinician. For instance, the report may include a likelihood of a subject being in a particular state, such as given brain state underlying a burst suppression pattern. In addition, indicators related to tracked complexity of burst dynamics may also be provided to a clinician for use, for example, in assessment of coma recovery, a depth of anesthesia, or evaluation of brain development in early neonates.

As previously described, local cortical dynamics in the state of burst suppression, as induced by propofol-induced general anesthesia, illustrate that (1) bursts and suppressions can occur in a limited cortical region while continuous activity persists in other areas; (2) even when all of cortex undergoes a 'global' burst, there may be significant differences in the timing of onset of bursts between disparate cortical regions, (3) that, within each burst, the frequency structure may match the brain state that was present prior to the onset of burst suppression; and (4) this frequency structure can change through the course of each burst. Taken together, these findings suggest that burst suppression is highly dependent on local cortical dynamics, as the state evolves both across time and across different cortical areas.

In one example, systems and methods, as described could also be used, for example, to detect anoxic brain injury sustained during the procedure. This information would then prompt appropriate clinical intervention that could include, for instance, measures to sustain or deepen cooling to provide protection from further injury.

In another example, a patient undergoing burst suppression to treat epilepsy could also be monitored using systems and methods, as described. For instance, one approach may include analysis of the dynamics of bursts of such epilepsy patient. Both the spectral content of the burst and the temporal patterns of the burst could be analyzed and compared to a reference set to determine whether any signatures of seizure activity are present. In addition, the spatial distribution of the bursts could be analyzed to infer whether the brain is in a homogeneous state or in differential local states of epilepsy and/or burst suppression. For instance, epileptiform activity might be present in only one part of the brain. This can be seen in FIG. 11, where seizure activity is present only on EEG channels on the patient's right side.

FIG. 12 also shows several examples where epileptiform activity within bursts is confined to a few specific channels, indicated by the asterisks and arrows. These burst dynamics could be characterized in a variety of ways, including spectral analysis (FIG. 11, FIG. 9, FIG. 10), or time domain characterizations that identify the presence of epileptic waveforms (FIGS. 11 and 12). A number of spatial analyses could be used, such as principal component analysis (FIG. 8), displays of burst or seizure amplitude across channels (FIG. 6A), displays of burst suppression probability (FIG. 5D) and its variability (FIG. 5E) across channels, all of which could be plotted relative to a patient's brain anatomy (FIG. 5A) or scalp. This information could be used to assist in deciding whether seizure activity is present (current state) and/or in deciding whether to lift the pharmacologically induced coma, providing a prognosis of the expected brain state once burst suppression subsides (future state).

In yet another example, a patient in burst suppression due to brain injury or coma could also be monitored using systems and methods, as described. Specifically, the spatial distribution of the bursts could be evaluated in order to assess the integrity of different brain areas, and the propagation of bursts could be used to infer whether brain connectivity has been altered. The spatial extent of the bursts could be characterized in a number of different ways, including principal component analysis (FIG. 8), displays of burst amplitude across channels (FIG. 6A), displays of burst suppression probability (FIG. 5D) and its variability (FIG. 5E) across channels, all of which could be displayed, say, relative to a patient's brain anatomy (FIG. 5A) or scalp. In some aspects, such information could be used to infer the spatial localization of the brain injury, and possibly assist in diagnosing the cause of the coma.

In addition, the spatial propagation of bursts could be characterized in a number of different ways, for instance by examining the onset time of bursts as a function of spatial location (FIG. 6A, 7A, 7B), or by considering the probability of a simultaneous burst as function of distance between electrodes (FIG. 7C). Such information could be used to infer the severity of the brain injury in terms of impaired brain connectivity, and possibly assist in diagnosing the cause of the coma. The proportion of channels or brain regions involved in burst suppression could be characterized using a histogram (FIG. 6B), where an increased participation of channels or brain areas would be signified by shift in the histogram to the right, while a decreasing level of participation would be signified by a shift in the histogram to the left. If a large proportion of the brain remains in burst suppression, with little change in underlying dynamics, this might suggest a poor state and poor prognosis. On the other hand, if large portions of the brain have recovered from burst suppression and show temporal and frequency structure, this might suggest an improving state and good prognosis. As discussed earlier, the temporal and frequency content within the burst could be used to assist with prognosis, as the complexity of the dynamics within the burst could be used to infer the brain state that would be present if the patient were not in burst suppression.

For instance, FIG. 9 shows how during general anesthesia, bursts show frontal alpha waves characteristic of general anesthesia before entering burst suppression. The frequency of the frontal alpha wave decreases through the course of each burst (FIG. 10). In a similar fashion, for coma patients, the within-burst dynamics could be evaluated, and changes in these dynamics could be used to assess the state of a coma patient, evaluate the rate of recovery, and establish a prognosis. The size of the bursts, as shown in FIGS. 13F and 14F, could also be used to indicate the level of brain activity during bursts, providing similar diagnostic and prognostic information. Overall, such information could then be used to determine the extent to which burst suppression has receded, to assist with predicting the patient's future state, or to assist with selecting additional treatments, or withdrawing treatment if the prognosis is very poor.

The above-described systems and methods may be further understood by way of additional examples. These examples are offered for illustrative purposes only, and is not intended to limit the scope of the present disclosure in any way. Indeed, various modifications of the disclosure in addition to those shown and described herein will become apparent to those skilled in the art from the foregoing description and the following examples and fall within the scope of the appended claims. For example, specific examples of brain states, medical conditions, levels of anesthesia or sedation and so on, in association with specific drugs and medical procedures are provided, although it will be appreciated that other drugs, doses, states, conditions and procedures, may be considered within the scope of the present disclosure. Furthermore, examples are given with respect to specific indicators related to brain states, although it may be understood that other indicators and combinations thereof may also be considered within the scope of the present disclosure. Likewise, specific process parameters and methods are recited that may be altered or varied based on variables such as signal amplitude, phase, frequency, duration and so forth.

EXAMPLES

Data Acquisition

Five patients with epilepsy intractable to medication, who were implanted with intracranial electrocorticography (ECoG) electrodes for standard clinical monitoring (AdTech Inc, Racine Wis.). Informed consent was obtained from all patients in accordance with the local institutional review board. Electrode placement was determined solely by clinical criteria. One patient was implanted only with depth electrodes and the other four had a combination of depth electrodes and subdural grid and strip electrodes, with 1 cm spacing between electrode contacts. Recordings were collected throughout induction of general anesthesia using propofol, at the beginning of a surgery to explant the electrodes. A portion of one recording from one patient was previously reported in a separate analysis of slow oscillations. ECoG data was recorded with a sampling rate of 2000 Hz, lowpass filtered at 100 Hz and resampled to 250 Hz. For all analyses of spatial dynamics (FIGS. 5-8), grid channels were referenced with a Laplacian montage in that the average of all available neighboring channels (up to four nearest neighbors) was subtracted, in order to minimize spatial spread of the signals. When analyzing temporal structure across all channels (grid, strip, and depth electrodes; FIGS. 9-10), they were referenced in a bipolar scheme as the depth and strip electrodes were positioned in 1-dimensional arrays. Channels with large artifacts or with periods of signal saturation were excluded from the analysis. All data were exported to Matlab (Mathworks) for further analysis with custom software.

Segmentation of Burst Suppression

In each patient, a period of burst suppression was manually identified and extracted for further analysis. An automated method to segment bursts and suppressions was used. The method first required manual labeling of unambiguous suppression periods in the first 60 seconds of the recording. The data was then transformed in three steps: 1) signals were high-pass filtered with a finite impulse response filter of length 2206, with a gain of 0 from 0-2.55 Hz and a gain of 1 from 3-125 Hz. 2) the Hilbert transform of the transformed signal was used to calculate the instantaneous amplitude, and 3) the instantaneous amplitude was smoothed with a moving average filter with a span of 50 samples (200 ms). These transformations yielded a continuous measure approximating high-frequency power. The value of this measure during the manually labeled suppression periods was used to set a threshold for burst detection (mean plus four standard deviations of the value during manually-labeled suppressions). Threshold crossings lasting over 500 ms were labeled as bursts, and burst terminations were labeled when the measure returned below threshold for 500 ms. 500 ms was used as a computational requirement for threshold crossings but manually confirmed that our method successfully detected the slow timescale shifts characteristic of burst suppression. In particular, the median duration of suppressions was 4.76 s, with an inter-quartile range of 3.76-7.31 s. To ensure that the results on burst timing were not an artifact of the burst detection algorithm, an alternative variance-based method was implemented. In this method, the variance of the raw signal was computed in 100 ms sliding windows and this measure replaced the instantaneous amplitude as the segmentation threshold.

Comparisons of Burst Timing

The difference in burst onset times was taken between every pair of electrodes in the grid. For each burst onset in a given electrode, the burst occurring closest in time in every other electrode was selected if it occurred within 1 s of the first burst. The absolute value of this timing difference was then calculated, and averaged across all pairs of electrodes in the grid. Timing differences were statistically compared across different distances of electrode separation using the Wilcoxon rank-sum test.

The joint probability of bursting in two electrodes was computed for each pair of electrodes by calculating the amount of time that both electrodes were simultaneously in a burst state, and then normalizing by the total amount of time that either electrode was in a burst state. As above, significant changes in joint bursting probability at different distances were calculated using the Wilcoxon rank-sum test.

Identification of Local Bursts

Burst onsets were plotted across all channels and found that burst onsets were visibly clustered across channels, enabling an automated selection of multichannel bursts using a simple threshold. Clusters of burst onsets were identified when at least 5 channels had a burst onset within a 200 ms bin. The number of channels involved in each burst was then computed by counting the number of channels that demonstrated a burst onset within 1.5 seconds of the main cluster, to ensure that all channels were counted even if burst onset was substantially delayed.

Spectral Analysis of Bursts

The spectral content of bursts was analyzed using multi-taper spectral estimation, computed with the Chronux toolbox. Within-burst dynamics were analyzed by selecting bursts lasting at least 3 seconds, and running a triggered spectral analysis at the onset of those bursts. Spectra were estimated with a T=2-second window, a time-bandwidth product of TW=3, and 5 tapers, yielding a spectral resolution of 1.5 Hz. An analogous calculation was performed on the baseline awake period by taking a triggered spectrum of an equal number of windows spaced 4 seconds apart. Error bars were computed as the standard error of the spectra across channels.

Comparisons of early and late portions of the burst were performed by selecting bursts lasting at least 3 seconds, and dividing them into two 1.5-second windows, marked 'early' and 'late'. The analysis was restricted to channels with an alpha peak, defined as channels where the maximum power in the 8-14 Hz range was higher than the maximum power in the 4-7 Hz range. For each portion, the spectrum was calculated in a T=1.5 second window, with time-bandwidth product TW=4, with 7 tapers, yielding a spectral resolution of 2.67 Hz. The peak alpha power was then identified as the frequency with the highest power lying between 8 and 14 Hz. Statistical testing was performed by identifying the difference between the early and late peak in each channel, and then performing a Wilcoxon signed-rank test on the difference across all channels. Plots show the average power across channels and error bars show the standard error.

These findings suggest a conceptual shift in how neurologists could assess the brain function of patients undergoing burst suppression. First, analyzing spatial variation in burst suppression could provide insight into the circuit dysfunction underlying a given pathology, and could improve monitoring of medically-induced coma. Second, analyzing the temporal dynamics within a burst could help assess the underlying brain state. This approach could be explored as a prognostic tool for recovery from coma, and for guiding treatment of status epilepticus. Overall, these results suggest new research directions and methods that could improve patient monitoring in clinical practice.

Thus, the foregoing establishes that the neural dynamics within a burst reflect the brain state that was prior to burst suppression. In an intracranial EEG study, it was shown that the spectral content of bursts during propofol general anesthesia replicates that of lighter general anesthesia, so lifting burst suppression should lead to a lighter anesthetized state. In a scalp EEG study, it was shown that the dynamics within bursts in epileptic patients contain signatures of the seizure that would be present if burst suppression is lifted. In one case it was shown that the epileptiform patterns are followed by a full-blown seizure, confirming that our analyses reflect the underlying brain state. Also, it was established that burst suppression is spatially heterogeneous across the brain and there is strong evidence for this in intracranial EEG recordings. Spatial differences can be detected even in scalp EEG recordings.

Therefore, the present disclosure provides systems and methods for acquiring and analyzing physiological data for identifying brain states of a subject observed, for example, during deep general anesthesia and in many neurological conditions including traumatic brain injury and medically induced coma. By analyzing the spectral characteristics of, for example, EEG data associated with bursts, along with spatial characteristics of burst suppression across the brain, an underlying brain state can be inferred that would be present if there were no burst suppression.

Accurately identifying brain states of a subject allows clinicians to diagnose and treat neurological disorders, as well as guide the administration of medically induced coma, or other medical procedures. As described, an automated approach is provided herein whereby segmented bursts and burst suppression epochs within the EEG feedback are utilized. Specifically, bursts that are sufficiently long (for example greater than 1 second) can be identified and their dynamics extracted, including spectral features. The approach provided may be used for analyzing variations in burst suppression dynamics in different cortical regions to determine that regions are most profoundly inactivated. For example, during burst suppression induced by propofol general anesthesia, this method can accurately extract the features of lighter propofol general anesthesia. The dynamics of scalp EEG recordings within a burst can be tracked to reveal underlying epileptic activity. In addition, different brain regions can be tracked to identify and understand that isolated states of burst suppression occur, and that spatial differences can be observed in the scalp EEG to help determine and predict current and future brain states of a subject. Both temporal and spatial analysis of EEG during burst suppression can be used to identify underlying dynamics and pathology, and are useful for patient monitoring, EEG-based diagnostics of neurological condition, and prognostic tools to assess and predict recovery from coma.

Burst suppression has previously been viewed as a global phenomenon, with synchronous bursts occurring simultaneously across cortical areas. As described herein, high correlation of bursts across cortex have been observed, demonstrating that, on average, bursts are broadly synchronous. However, substantial local variation in burst dynamics has also been identified. Burst timing differs consistently across cortex, with larger timing offsets between bursts in distant regions. In addition, both bursts and suppressions frequently occur locally, limited to a small cluster of electrodes while other cortical regions were in a different state. One possible explanation for this could be local variation in cerebral metabolism: when metabolism is globally depressed, bursts can spread across cortex, producing a gradient of timing differences; whereas when metabolic rates are more varied in different regions, they may enter dissociated states with different burst suppression probabilities and different refractory periods, leading to spatially isolated bursts and suppressions. This interaction could resolve the contrast inherent in these results, as this mechanism would produce dynamics which bursts are often correlated but can nevertheless demonstrate substantial local variation.

Although a number of systems exist that can monitor the presence of burst suppression in the EEG and measure the burst-suppression ratio, these systems do not provide information about what the brain state would be once the patient were to recover from burst suppression. This information is helpful for assessing a patient's brain state, and for determining when to lift a medically-induced coma. By contrast, the present disclosure provides descriptions of systems that can extract features specifically within a burst, and use those to infer the underlying brain state. As described, it has been shown that burst suppression is a substantially heterogeneous state across the brain, so systems may uniquely incorporate information from multiple brain regions when assessing burst suppression.

Specifically, systems in accordance with the present disclosure can be embodied in a manner that may automatically analyze burst spectral content and display the results for anesthesiologists and neurologists to monitor patients' brain state. In addition, such systems can also be embodied as a diagnostic/prognostic tools that analyze burst spectral content and matches it against a library of known feature sets to provide a likelihood of which brain state underlies the burst suppression pattern, helping diagnosis and prognosis of patients in coma states. Moreover, such systems could also be used to signal to a clinician when it is safe to lift a medically-induced coma, as for example in treatment of status epilepticus or traumatic brain injury.

Thus, among others, the present disclosure provides system and methods for determining cortical dynamics underlying burst suppression and spatiotemporal properties related thereto. This information can be used to determine the spatial distribution of burst suppression across the cortex Identifying, for example, that the temporal structure of the state preceding burst suppression can be replicated in bursts and decelerates throughout bursts, preceding and future states can be predicted. The present disclosure recognizes that patients who enter burst suppression while receiving propofol general anesthesia experience bursts that are substantially asynchronous across the cortex by recording intracranial EEGs, and the state of burst suppression occurs in a limited cortical region while other areas exhibit ongoing continuous activity. In addition, the present disclosure recognizes that even when all of the cortex undergoes a 'global' burst, there are significant differences in the timing of onset of bursts between disparate cortical regions, that, within each burst, the frequency structure matches the brain state that was present prior to the onset of burst suppression.

In addition to monitoring spectral dynamics within a burst, the spatial heterogeneity of burst suppression has implications for understanding of neurological disease, and could impact clinical treatment. First, results presented herein indicate that patients exhibiting burst suppression may in fact have substantial local variation in brain function. Neurologists may therefore wish to examine spatial differences in burst suppression to ascertain whether specific cortical regions are more susceptible to circuit dysfunction, as inactivation in different brain structures may be a function of underlying pathology. Furthermore, these results suggest that medically-induced coma, as used for treatment of status epilepticus and traumatic brain injury, could be monitored across multiple cortical regions and the treatment adjusted accordingly, as dynamics in one brain region may not fully reflect the ongoing state. In addition, the ability to observe and characterize local expression of suppression epochs could allow for more precise tracking of anesthetic induction and emergence, and of hypothermia induced during surgery. Specialized monitoring systems, in accordance with the present disclosure, could be designed, for example, to exploit EEG spatial patterns in order to facilitate superior control of drug dosages when inducing burst suppression to control status epilepticus or for treatment of traumatic brain injury, ensuring that a desired burst suppression ratio is achieved throughout the brain rather than at a single cortical site.

Examples presented herein are consistent with the neuronal and metabolic mechanisms proposed in recent computational work, that has suggested that lowered cerebral metabolism leads to periods of suppression, but that the activity within each burst recovers the oscillatory dynamics of the state preceding burst suppression. An alternative hypothesis is that bursts are due to cortical hyperexcitability. In the case of propofol general anesthesia, the EEG prior to burst suppression contains two distinct rhythms: a slow (i.e., 0.1-1 Hz) oscillation that is asynchronous across cortex, and an alpha (i.e., ~10 Hz) rhythm that is highly coherent across frontal electrodes. The slow oscillation contains EEG deflections that mark brief (<1 s) periods of local cortical neuron inactivation. These inactivated periods occur both during sleep and general anesthesia, and correlate with loss of consciousness. The present disclosure has found that bursts indeed replicated the EEG signatures of lighter stages of general anesthesia: they exhibited both a slow oscillation and a frontal alpha oscillation that decelerated throughout the burst, as predicted by the decreased cerebral metabolism model. Because slow oscillations were contained within bursts suggests that burst suppression may be due to prolonged epochs of suppression overriding the ongoing cortical state. Bursts would then reflect a transient recovery in that the oscillatory rhythms characteristic of the preceding state (i.e. the slow and alpha oscillations) resume. This theory is additionally consistent with the fact that patients remain anesthetized during bursts, as their EEG continues to reflect the signatures of propofol general anesthesia. Therefore, the main emergent feature of burst suppression may in fact be the suppression, that acts as an intermittent but prolonged interruption of ongoing cortical activity. The burst content could then serve as a readout of the previous cortical state, that could provide useful clinical information when monitoring patients during burst suppression.

The spatial heterogeneity observed is also consistent with the metabolic model. In particular, it would follow from the model that bursts and suppressions may be shorter or longer in different brain regions depending on regional variations in perfusion, local network activity, ATP concentration, and metabolic state. These spatial results are also compatible with a calcium-based mechanism for burst suppression. Namely, it has been suggested that transient increases and decreases in extracellular calcium, leading to synaptic disfacilitation, are a key determinant in suppression duration. Again, such a mechanism would naturally lead to local variability due to calcium distribution and expression. Taken together, the present disclosure supports a model in that burst suppression is driven by local variations in cortical dynamics, and are consistent with the hypothesis that suppressions are caused by decreased cerebral metabolism.

Although data presented herein, by way of example, is the result of studies focused on the cortical dynamics of burst suppression, subcortical structures, however, may also be a determinant in the expression of burst suppression in the brain. The local differences shown in cortical measurements are suggestive of nontrivial subcortical participation in each burst and suppression. The state of burst suppression can be viewed as a severe reduction in the ability of cortical neurons to sustain continued processing. Whether the reason is protective, for instance by metabolic mechanisms, or otherwise, the neurons in question simply cannot fire for prolonged periods of time. In contrast, previous research on the cellular correlates of burst suppression has shown that certain subcortical populations, namely thalamic reticular and relay cells, may exhibit ongoing activity even during cortical suppressions. The generation of individual bursts is thought to be caused by input from these relay neurons once cortical post-suppression refractory periods subside. The extent to which burst suppression is expressed differentially in the cortex may thus be a reflection of the integrity of specific thalamocortical networks. In this scenario, the dynamic range in some subcortical loops, and the efficacy of ascending and descending excitation, can remain largely intact, despite existing in a significantly inactivated brain. These differences suggest that there are differential sensitivities of cortical regions and their associated functions to anesthetic drugs at high concentrations, hypothermia and diffuse brain injury.

Hence, the present disclosure provides for new insight into the neurophysiology of the profoundly inactivated brain. Despite trends towards synchronous activity, local cortical dynamics vary across time and space, and can lead to uncoupled burst suppression states across cortex. Results presented demonstrate previously unknown complexity in neural circuit dynamics during deep general anesthesia, and suggest new roles for cortical and subcortical structures in producing neurophysiological diversity during profound neural inactivation. These findings indicate that burst suppression in neurological conditions can benefit from examination of how cortical activity varies within bursts and across electrodes, as these dynamics may be highly variable.

In this manner, spatiotemporal structure of burst suppression patterns could improve patient monitoring and the effectiveness of clinical treatments.

Given that burst suppression can be both a symptom of neurological conditions (i.e., in post-anoxic coma) as well as the result of induced treatment for conditions such as status epilepticus and traumatic brain injury, findings, as described herein, could have significant impact on clinical practice. In particular, detection of the spectral content within each burst could reveal the neural dynamics that remain intact when not interrupted by the suppression epochs. For instance, bursts may contain activity synonymous with general anesthesia as observed here, or they could be morphologically similar to epileptiform patterns associated with seizure.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for monitoring a subject, the system comprising:
   a plurality of electroencephalogram (EEG) sensors configured to acquire EEG signals from multiple locations about a subject's brain;
   an input configured to receive at least the EEG signals from the plurality of EEG sensors;
   a processor in communication with the input and configured to:
      i) receive the EEG signals from the input;
      ii) assemble a set of time-series data using the EEG signals received;
      iii) analyze the set of time-series data to identify burst or burst suppression epochs corresponding to a burst suppression state;
      iv) identify a burst characteristic profile for the subject based on a burst pattern determined from the epochs identified in (iii), wherein the burst pattern represents spatial and temporal occurrences of bursts across cortical regions of the subject's brain;
      v) compare the burst characteristic profile against a reference set of burst profiles; and
      vi) determine, based on the comparison of (v), a likelihood of a brain state of the subject underlying the burst suppression state; and
   a display configured to provide a report, generated by the processor, indicating the likelihood of the brain state determined in (vi).

2. The system of claim 1, wherein the processor is further configured to apply a segmentation algorithm to identify the epochs in the set of time-series data.

3. The system of claim 1, wherein the burst characteristic profile includes a burst spectral content.

4. The system of claim 1, wherein the processor is further configured to determine at least one of a burst timing pattern and a spatial pattern using the burst activity across the subject's brain.

5. The system of claim 1, wherein the reference set of burst profiles is related to a non-burst suppression state.

6. The system of claim 1, wherein the processor is further configured to generate and provide an indication in relation to a future brain state of the subject upon recovery from the burst suppression state.

7. The system of claim 1, further comprising a controller for controlling a future brain state of the subject using the determined brain state.

8. The system of claim 1, wherein the display is further configured to indicate a burst cluster illustrative of concurrent burst activity across the subject's brain.

9. A method for monitoring a subject comprising steps of:
   (a) acquiring electroencephalogram (EEG) signals from multiple locations about a subject's brain using a plurality of EEG sensors positioned thereabout; and
   using a processor
      (b) assembling a set of time-series data using the EEG signals acquired;
      (c) analyzing the set of time-series data to identify burst or burst suppression epochs corresponding to a burst suppression state;
      (d) identifying a burst characteristic profile for the subject based on a burst pattern determined from the epochs identified at step (c), wherein the burst pattern represents spatial and temporal occurrences of bursts across cortical regions of the subject's brain;
      (e) comparing the burst characteristic profile against a reference set of burst profiles;
      (f) determining, based on the comparison of step (e), a likelihood of a brain state of the subject underlying the burst suppression state; and
      (g) generating a report indicative of the likelihood of the brain state determined in step (f).

10. The method of claim 9, the method further comprising applying a segmentation algorithm to identify the epochs of the set of time-series data.

11. The method of claim 9, wherein the burst characteristic profile includes a burst spectral content.

12. The method of claim 9, the method further comprising determining at least one of a burst timing pattern and a spatial pattern using the burst activity across the subject's brain.

13. The method of claim 9, wherein the reference set of burst profiles is related to a non-burst suppression state.

14. The method of claim 9, the method further comprising providing an indication in relation to a future state of the subject upon recovery from the burst suppression state.

15. The method of claim 9, the method further comprising indicating a burst cluster illustrative of concurrent burst activity across the a subject's brain.

16. The method of claim 9, the method further comprising controlling a future brain state of the subject using the determined brain state.

* * * * *